US012718386B2

(12) United States Patent
Holst et al.

(10) Patent No.: US 12,718,386 B2
(45) Date of Patent: Aug. 25, 2026

(54) SYSTEMS, DEVICES, AND METHODS FOR GENERATING DATA SERIES TO VISUALIZE QUANTITATIVE STRUCTURE DATA REGISTERED TO IMAGING DATA

(71) Applicant: Augmedics, Inc., Arlington Heights, IL (US)

(72) Inventors: John Holst, La Jolla, CA (US); Alejandro Sklar, Pittsburgh, PA (US); Emmanuel Nunez, Houston, TX (US)

(73) Assignee: Augmedics, Inc., Arlington Heights, IL (US)

(*) Notice: Subject to any disclaimer, the term of this patent is extended or adjusted under 35 U.S.C. 154(b) by 380 days.

(21) Appl. No.: 18/184,573

(22) Filed: Mar. 15, 2023

(65) Prior Publication Data

US 2024/0312032 A1 Sep. 19, 2024

(51) Int. Cl.
*G06T 7/30* (2017.01)
*A61B 5/00* (2006.01)
(Continued)

(52) U.S. Cl.
CPC .............. *G06T 7/30* (2017.01); *A61B 5/4566* (2013.01); *G06T 7/0012* (2013.01); *G16H 30/20* (2018.01);
(Continued)

(58) Field of Classification Search
CPC ............. G06T 2207/20084; G06T 7/11; G06T 7/0012; G06T 2207/20081; G06T 2207/30012; G06T 2207/30008; G06T 7/75; G06T 2207/30004; G06T 7/12; G06T 7/33; G06T 2207/30196; G06T 2210/41; G06T 7/344; G06T 7/30; G06T 2207/20021; G06T 2207/30016;
(Continued)

(56) References Cited

U.S. PATENT DOCUMENTS 8,160,676 B2 * 4/2012 Gielen ..................... A61B 5/06 600/407
8,891,848 B2 * 11/2014 Blumfield .............. G16H 30/20 382/128

(Continued)

OTHER PUBLICATIONS

B. De Leener, J. Cohen-Adad and S. Kadoury, "Automatic Segmentation of the Spinal Cord and Spinal Canal Coupled With Vertebral Labeling," in IEEE Transactions on Medical Imaging, vol. 34, No. 8, pp. 1705-1718, Aug. 2015, doi: 10.1109/TMI.2015.2437192. (Year: 2015).*

*Primary Examiner* — Courtney Joan Nelson
(74) *Attorney, Agent, or Firm* — Dinsmore & Shohl LLP

(57) ABSTRACT

Embodiments include example systems, methods, and computer-accessible mediums for analysis and visualization of data associated with anatomical images. In some embodiments the anatomical images can be spinal images used for assessment of stenosis and disc degeneration. In some embodiments, systems, devices, and methods described herein include selecting a region of interest (ROI) in a three-dimensional (3D) volume of image data of a plurality of vertebra of a spine, identifying one or more anatomical parts in the ROI, determining one or more parameters of the one or more anatomical parts, and assessing a severity of a spinal deformity based on the one or more parameters.

20 Claims, 42 Drawing Sheets
(37 of 42 Drawing Sheet(s) Filed in Color)

(51) Int. Cl.

| | |
|---|---|
| ***G06T 7/00*** | (2017.01) |
| ***G16H 30/20*** | (2018.01) |
| ***G16H 30/40*** | (2018.01) |

(52) U.S. Cl.

CPC ... *G16H 30/40* (2018.01); *G06T 2207/20021* (2013.01); *G06T 2207/20081* (2013.01); *G06T 2207/20084* (2013.01); *G06T 2207/30012* (2013.01); *G06T 2207/30016* (2013.01)

(58) Field of Classification Search

CPC ........ G16H 30/40; G16H 50/20; G16H 30/20; G16H 50/30; G16H 50/50; G06N 3/08; G06N 20/00; G06N 3/02; A61B 6/505; A61B 34/10; A61B 6/5205; A61B 2576/02; A61B 2034/105; A61B 5/4566; A61B 34/20; A61B 5/7264; A61B 8/0875; A61B 8/469; A61B 8/5223; A61B 2034/101; G06F 18/214; G06V 20/64; G06V 2201/033; G06V 10/82; G06V 2201/03

See application file for complete search history.

(56) References Cited

U.S. PATENT DOCUMENTS

| | | | | |
|---|---|---|---|---|
| 9,020,235 | B2 * | 4/2015 | Krishnan | A61B 6/469 382/132 |
| 9,408,584 | B2 * | 8/2016 | Major | A61B 6/032 |
| 10,325,068 | B2 * | 6/2019 | Ayed | G16H 30/40 |
| 10,417,768 | B2 * | 9/2019 | Yu | G06F 18/2413 |
| 2007/0174769 | A1 * | 7/2007 | Nycz | G06F 3/04845 715/700 |
| 2020/0113524 | A1 * | 4/2020 | Benson | G16H 50/20 |
| 2020/0320786 | A1 * | 10/2020 | Kadoury | G06T 7/0012 |
| 2023/0206662 | A1 * | 6/2023 | Masuzawa | G06V 10/86 382/128 |

* cited by examiner 662
664a
664b
664c

SYSTEMS, DEVICES, AND METHODS FOR GENERATING DATA SERIES TO VISUALIZE QUANTITATIVE STRUCTURE DATA REGISTERED TO IMAGING DATA

TECHNICAL FIELD

The present disclosure relates generally to systems, devices, and methods for spine analysis, and specifically relates to analyzing anatomical image data for spinal deformity assessment.

BACKGROUND

A person's spinal column is a complex system of bones and soft tissue structures. The spine, which forms part of the spinal column, functions as the body's central support structure, and is composed of many individual bones known as vertebrae. Intervertebral discs are positioned between adjacent vertebrae to provide support and cushioning between the vertebrae. The vertebrae and intervertebral discs, together with other soft tissue structures (e.g., ligaments, nervous systems structures, etc.) in their vicinity, form the spinal column. Each intervertebral disc is made up of a dense series of collagen layers called annulus fibrosis and a hydrogel comprising proteoglycan and water called the nucleus. Dehydration of the intervertebral disc (e.g., dehydration of annulus fibrosis and/or dehydration of nucleus) due to age and other factors can lead to loss of structural and functional integrity of the intervertebral disc referred to as "disc degeneration." Nerve roots exit the spine through an opening between two adjacent vertebrae. The opening is called the intervertebral foramen. An abnormal narrowing of the intervertebral foramen can lead to spinal stenosis. Changes to tissues and/or bones can lead to other spinal deformities such as disc herniation, osteophyte formation, spondylolisthesis, etc.

Spinal deformities or diseases can take many forms. Two common ones are spinal stenosis and degenerative disc disease. Spinal stenosis involves a narrowing of the central canal of the spine. One example of spinal stenosis is degenerative lumbar spinal stenosis (DLSS). DLSS is a major cause of low back pain and is one of the most common indications for spinal surgery. In the working-age population, e.g., particularly in males between 40 and 50 years of age, DLSS has a high prevalence rate and can cause high medical and/or societal cost. Disc degeneration occurs as a result of changes in an individual's intervertebral discs. Degenerative disc disease can also lead to lower back pain, which affects young to middle-aged persons with peak incidence at approximately 40 years old. Disc degeneration can also lead to sciatica.

FIG. 11 depicts the progression of degenerative disc disease. Typically disc degeneration is a cascade of events originating from loss of hydration of the disc, which can lead to altered mechanical strains on the nucleus and annulus, and can result in a variety of consequences including: loss of disc height (e.g., disc narrowing or thinning), which can narrow the intervertebral foramen where the spinal nerve exits the spine: disc bulging or herniation, which also narrows the space for the spinal nerve; and other instabilities or deformities. When such instability occurs, the body may react to it by growing bone across the joint, in a process known as "autofusing." In particular, the body can grow bone spurs or osteophytes around the disc and/or facet joints. The growth of osteophytes can further complicate the negative effects of disc degeneration.

Spinal assessment can enable detection of various spinal conditions and/or spinal deformities. Detecting and treating spinal conditions and/or spinal deformities at an early stage (e.g., when the condition is mild) can prevent the conditions from becoming severe. When conducting spinal assessment, it can be important to identify the specific location, geometric limits, and other parameters within the spine. These parameters can be indicative of the type of spinal condition and/or spinal deformity and its location within the spine. Analyzing image data of a person's anatomy can help identify existing spinal conditions and/or spinal deformities. Some existing imaging systems include, for example, computed tomography (CT), magnetic resonance imaging (MRI), X-ray, ultrasound, and fluoroscopy systems. Such imaging is widely utilized for both initial diagnosis and follow up evaluation in both conservative and surgical treatment pathways.

Traditional X-ray and CT are common methods for acquiring information of patient anatomy, including, for example, a spine of the patient. Traditional X-rays involve directing high-energy electromagnetic radiation at a patient's body, and capturing a resulting two-dimensional (2D) X-ray profile on a film or plate. X-ray imaging, however, can subject patients to high levels of radiation. Analysis of X-rays can also be subjective based on physician training and experience. Currently, there is no autonomous way to objectively analyze X-rays. Accordingly, performing necessary measurement on X-rays requires time and can be subject to user error. Lack of autonomous methods of analyzing X-rays also makes it difficult to objectively compare a patient's X-rays over time, e.g., to track a patient's progress. Due to these limitations, it is not presently possible to reliably predict certain outcomes based on X-ray imaging. It is also not presently possible to obtain necessary measurements in an autonomous and/or consistent fashion that ensures reliability and reproducibility of such measurements.

CT involves using controlled amounts of X-ray radiation to obtain 3D image data of patient anatomy. Existing CT systems can include a rotating gantry that has an X-ray tube mounted on one side and an arc-shaped detector mounted on an opposite side. An X-ray beam can be emitted in a fan shape as the rotating frame spins the X-ray tube and detector around a patient. Each time the X-ray tube and detector make a 360° rotation and the X-ray passes through the patient's body, an image of a thin section of the patient anatomy can be acquired. During each rotation, the detector can record about 1,000 images or profiles of the expanded X-ray beam. Each profile can then be reconstructed by a dedicated computer into a 3D image of the section that was scanned. Accordingly, CT systems use a collection of multiple 2D CT scans or X-rays to construct a 3D image of the patient anatomy. The speed of gantry rotation, along with slice thickness, contributes to the accuracy and/or usefulness of the final image. Commonly used intraoperative CT imaging systems have a variety of settings that allow for control of the radiation dose. In certain scenarios, high dose settings may be chosen to ensure adequate visualization of the anatomical structures. The downside is increased radiation exposure to the patient. The effective doses from diagnostic CT procedures are typically estimated to be in the range of 1 to 10 millisieverts (mSv). Such high doses can lead to increased risk of cancer and other health conditions. Low dose settings are therefore selected for CT scans whenever possible to minimize radiation exposure and associated risk of cancer development. Low dose settings, however, may have an impact on the quality of the image data available for the surgeon.

MRI imaging systems operate by forming a strong magnetic field around an area to be imaged. In most medical applications, protons (e.g., hydrogen atoms) in tissues containing water molecules produce a signal that is processed to form an image of the body. First, energy from an oscillating magnetic field is temporarily applied to the patient at an appropriate resonance frequency. The excited hydrogen atoms emit a radio frequency (RF) signal, which is measured by a RF system. The RF signal may be made to encode position information by varying the main magnetic field using gradient coils. As these coils are rapidly switched on and off, they produce the characteristic repetitive noise of an MRI scan. Contrast between different tissues can be determined by the rate at which excited atoms return to their equilibrium state. In some instances, exogenous contrast agents may be given intravenously, orally, or intra-articularly, to further facilitate differentiation between different tissues. The major components of an MRI imaging system are the main magnet that polarizes tissue, the shim coils for correcting inhomogeneities in the main magnetic field, the gradient system for localizing the magnetic resonance (MR) signal, and the RF system that excites the tissue and detects the resulting signal. With MRI imaging, different magnetic field strengths can be used. The most common strengths are 0.3T, 1.5T and 3T. The higher the strength, the higher the image quality. For example, a 0.3T magnetic field strength will result in lower quality imaging then a 1.5T magnetic field strength.

Currently, there is also no autonomous way of objectively analyzing MRI images, with analysis of such images being reliant on physician training and experience. Moreover, due to technical limitations, diagnostic MRI protocols provide a limited number of slices of a target region, which leaves a physician to piece together anatomical information from available axial, sagittal, and/or coronal scans of the patient anatomy. Existing systems also lack a reliable way to easily and autonomously compare a patient's MRI images against a larger database of MRI images. Such comparison can allow a physician to obtain additional information about the severity of a patient's condition. Existing systems also lack the ability to autonomously compare a patient's MRI images at a present time against past images of that patient. In addition, it is not currently possible to screen a patient's MRI images for spinal cord compression, fracture, tumor, infection, among other conditions. Such limitations make it difficult if not impossible to make treatment recommendations based on patient MRI images that would result in a high degree of confidence in treatment outcome.

Even with these limitations, MRI is typically the imaging of choice for assessing spinal stenosis due to its ability to image soft tissue details. MRI also provides anatomical information that enables radiologists to identify the location, etiology and severity of the nerve root compression and report their findings. However, interpretation of MRIs of spinal anatomy can be time consuming, especially when advanced multi-level degeneration is present. While there exists imaging-based grading systems such as the Lee grading or Pfirrmann grading systems, the inter-reader variability, even among specialists, is high and degrades the perceived value of a reader's reporting. Therefore, a solution that provides an accurate and consistent interpretation of imaging data for stenosis, that can be applied at scale, has high clinical utility.

Similarly, for assessing disc pathology and degeneration, MRI is commonly used due to its lack of radiation, multiplanar imaging capability, high spinal soft tissue contrast, and precise localization of intervertebral discs changes. In some cases, antero-posterior (AP) and lateral views of X-rays can also be helpful in visualizing gross anatomic changes in the intervertebral disc. However, MRI is the standard imaging modality for detecting disc pathology because its aforementioned advantages present high clinical value in providing a clinician with information about disk degeneration.

With low quality images and lack of reliable and/or reproducible image analysis, existing systems pose a diagnostic challenge for physicians. Such limitations can make it difficult to adequately identify key landmarks and conduct measurements. This in turn can make it difficult to accurately conduct spinal assessment to detect spinal conditions and/or spinal deformities. Accordingly, additional systems, devices, and methods for spinal analysis to detect spinal conditions and/or spinal deformities may be desirable. In particular, a solution that provides an accurate and consistent interpretation of imaging data, especially MRI imaging data, is desirable.

SUMMARY OF DISCLOSURE

Systems, devices, and methods described herein relate to analysis of anatomical images and identification of anatomical components and/or structures. In some embodiments, systems, devices, and methods described herein relate to identification of spinal conditions and/or spinal deformities.

In some embodiments, a method includes: selecting a region of interest (ROI) in a three-dimensional (3D) volume of image data of a plurality of vertebra of a spine, the ROI including image data of one or more vertebra from the plurality of vertebra and tissue structures surrounding the one or more vertebra: identifying a spinal cord or thecal sac in the ROI: determining one or more parameters associated with the spinal cord or thecal sac in the ROI; and determining a severity of spinal stenosis in the ROI based on the one or more parameters associated with the spinal cord or thecal sac.

In some embodiments, an apparatus includes: a memory; and a processor operatively coupled to the memory, the processor configured to: select a region of interest (ROI) in a three-dimensional (3D) volume of image data of a plurality of vertebra of a spine, the ROI including image data of one or more vertebra from the plurality of vertebra and tissue structures surrounding the one or more vertebra: identify a spinal cord or thecal sac in the ROI; determine one or more parameters associated with the spinal cord or thecal sac in the ROI; and determine a severity of spinal stenosis in the ROI based on the one or more parameters associated with the spinal cord or thecal sac.

In some embodiments, anon-transitory processor-readable medium storing code representing instructions to be executed by a processor, the code comprising code to cause the processor to: select a region of interest (ROI) in a three-dimensional (3D) volume of image data of a plurality of vertebra of a spine, the ROI including image data of one or more vertebra from the plurality of vertebra and tissue structures surrounding the one or more vertebra: identify a spinal cord or thecal sac in the ROI: determine one or more parameters associated with the spinal cord or thecal sac in the ROI; and determine a severity of spinal stenosis in the ROI based on the one or more parameters associated with the spinal cord or thecal sac.

In some embodiments, a method includes: selecting a region of interest (ROI) in a three-dimensional (3D) volume of image data of a plurality of vertebra of a spine, the ROI including image data of one or more vertebra from the plurality of vertebra and tissue structures surrounding the one or more vertebra: identifying one or more nerve roots in the ROI: tracking the one or more nerve roots from a lateral recess to a vertebral foramen of the one or more vertebra to identify one or more regions including a discontinuity in a nerve root or a narrowed section of a nerve root; and determining a severity or a location of spinal stenosis in the ROI based on the one or more regions.

In some embodiments, an apparatus includes: a memory; and a processor operatively coupled to the memory, the process configured to: select a region of interest (ROI) in a three-dimensional (3D) volume of image data of a plurality of vertebra of a spine, the ROI including image data of one or more vertebra from the plurality of vertebra and tissue structures surrounding the one or more vertebra: identify one or more nerve roots in the ROI: track the one or more nerve roots from a lateral recess to a vertebral foramen of the one or more vertebra to identify one or more regions including a discontinuity in a nerve root or a narrowed section of a nerve root; and determine a severity or a location of spinal stenosis in the ROI based on the one or more regions.

In some embodiments, a non-transitory processor-readable medium storing code representing instructions to be executed by a processor, the code comprising code to cause the processor to: select a region of interest (ROI) in a three-dimensional (3D) volume of image data of a plurality of vertebra of a spine, the ROI including image data of one or more vertebra from the plurality of vertebra and tissue structures surrounding the one or more vertebra: identify one or more nerve roots in the ROI: track the one or more nerve roots from a lateral recess to a vertebral foramen of the one or more vertebra to identify one or more regions including a discontinuity in a nerve root or a narrowed section of a nerve root; and determine a severity or a location of spinal stenosis in the ROI based on the one or more regions.

In some embodiments, a method includes: selecting a region of interest (ROI) in a three-dimensional (3D) volume of image data of a plurality of vertebra of a spine, the ROI including image data of one or more vertebra from the plurality of vertebra and tissue structures surrounding the one or more vertebra: identifying an intervertebral disc in the ROI: determining one or more parameters of an annulus and a nucleus of the intervertebral disc; and determining a disc degeneration ratio based on the one or more parameters of the annulus and the nucleus of the intervertebral disc.

In some embodiments, an apparatus includes: a memory; and a processor operatively coupled to the memory, the process configured to: select a region of interest (ROI) in a three-dimensional (3D) volume of image data of a plurality of vertebra of a spine, the ROI including image data of one or more vertebra from the plurality of vertebra and tissue structures surrounding the one or more vertebra: identify an intervertebral disc in the ROI: determine one or more parameters of an annulus and a nucleus of the intervertebral disc; and determine a disc degeneration ratio based on the one or more parameters of the annulus and the nucleus of the intervertebral disc.

In some embodiments, a non-transitory processor-readable medium storing code representing instructions to be executed by a processor, the code comprising code to cause the processor to: select a region of interest (ROI) in a three-dimensional (3D) volume of image data of a plurality of vertebra of a spine, the ROI including image data of one or more vertebra from the plurality of vertebra and tissue structures surrounding the one or more vertebra: identify an intervertebral disc in the ROI: determine one or more parameters of an annulus and a nucleus of the intervertebral disc; and determine a disc degeneration ratio based on the one or more parameters of the annulus and the nucleus of the intervertebral disc.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

1. Overview of System

Figure 1:
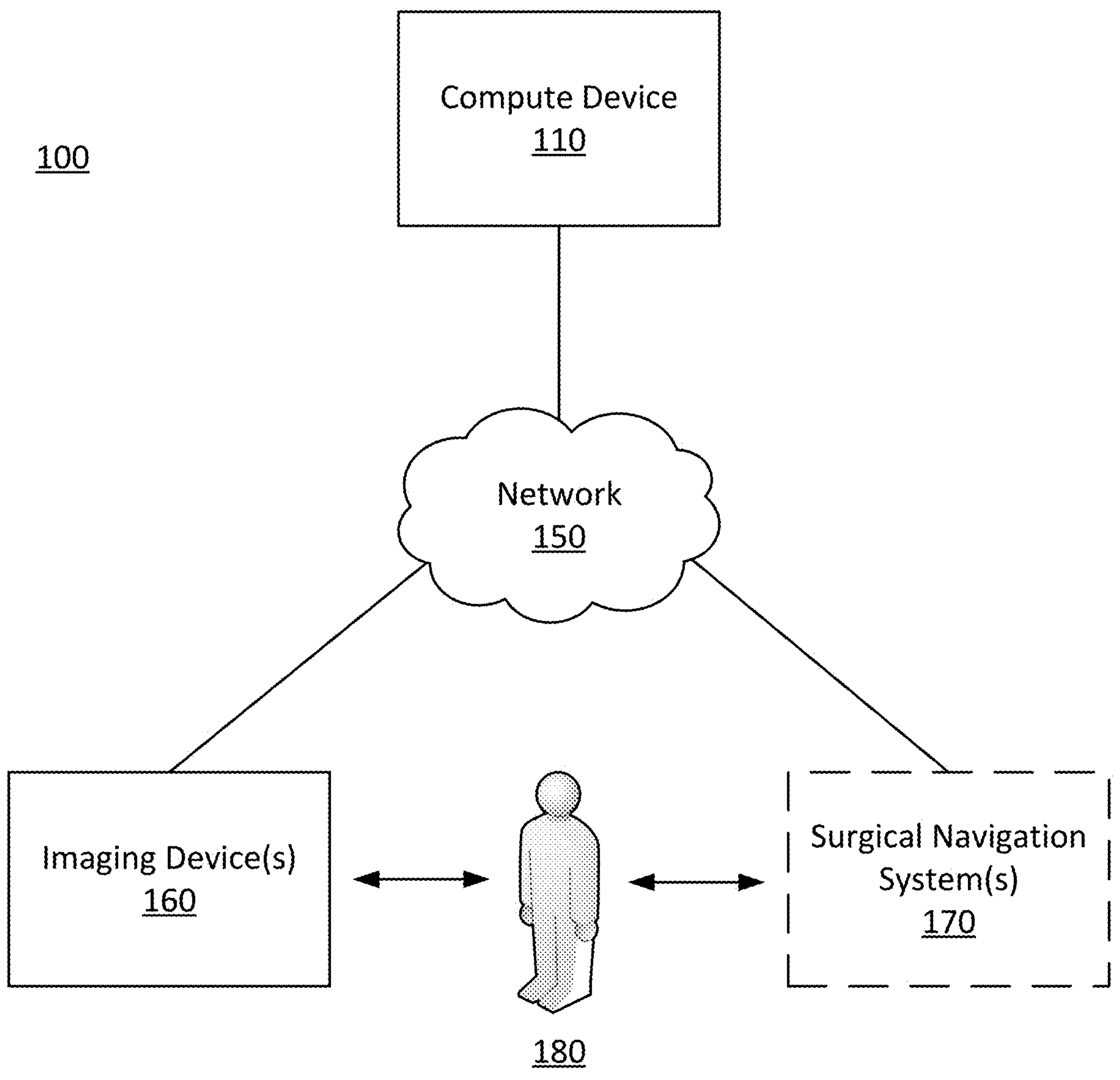
FIG. 1 is a block diagram illustrating a configuration of a system for collecting and analyzing anatomical images, according to some embodiments.

Systems, devices, and methods described herein relate to processing of patient anatomical structures, including a spine. While certain examples presented herein may generally relate to processing of image data of a spine, it can be appreciated by one of ordinary skill in the art that such systems, devices, and methods can be used to process image data of other portions of patient anatomy, including, for example, vessels, nerves, bone, and other soft and hard tissues near the brain, heart, or other regions of a patient's anatomy.

Systems, devices, and methods described herein can be suited for processing several different types of image data, including X-ray, computer tomography (CT), magnetic resonance imaging (MRI), fluoroscopic, ultrasound, etc. In some embodiments, such systems, devices, and methods can process a single image type and/or view, while in other embodiments, such systems, devices, and methods can process multiple image types and/or views. In some embodiments, multiple image types and/or views can be combined to provide richer data regarding a patient's anatomy.

Systems, devices, and methods described herein can implement machine learning models to process and/or analyze image data regarding a patient's anatomy. Such machine learning models can be configured to identify and differentiate between different anatomical parts within anatomical structures. In some embodiments, machine learning models described herein can include neural networks, including deep neural networks with multiple layers between input and output layers. For example, one or more convolutional neural networks (CNNs) can be used to process patient image data and produce segmentation outputs that classify different objects within the image data and/or identify different levels of the spine in the image data. Suitable examples of segmentation models and the use thereof are described in U.S. Patent Application Publication No. 2019/0105009, published Nov. 11, 2019, titled "Automated Segmentation Of Three Dimensional Bony Structure Images," U.S. Patent Application Publication No. 2020/0151507, published May 14, 2020, titled "Autonomous Segmentation Of Three-Dimensional Nervous System Structures From Medical Images," U.S. Patent Application Publication No. 2020/0410687, published Dec. 31, 2020, titled "Autonomous Multidimensional Segmentation Of Anatomical Structures On Three-Dimensional Medical Imaging," U.S. Provisional Patent Application No. 63/187,777, filed May 12, 2021, titled "Systems, Devices, and Methods for Segmentation of Anatomical Image Data," and PCT Patent Application No. PCT/US22/29000, filed May 12, 2022, titled "Systems, Devices, and Methods for Segmentation of Anatomical Image Data," the disclosures of each of which are incorporated herein by reference. Suitable examples of methods of level identification are described in U.S. Patent Publication No. 2020/0327721, published Oct. 15, 2020, titled "Autonomous Level Identification of Anatomical Bony Structures on 3D Medical Imagery," and U.S. Provisional Patent Application No. 63/256,306, filed Oct. 15, 2021, titled "Level Identification of Three-Dimensional Anatomical Images," the disclosures of each of which are incorporated herein by reference. While certain examples described herein employ CNNs, it can be appreciated that other types of machine learning algorithms can be used to process patient image data, including, for example, support vector machines (SVMs), decision trees, k-nearest neighbor, and artificial neural networks (ANNs).

In some embodiments, systems, devices, and methods described herein can implement machine learning models (e.g., spinal analysis model(s) as further described herein) to perform anatomical feature analysis and/or to perform spinal deformity diagnosis or classification. For example, systems, devices, and methods described herein can identify and differentiate between different anatomical parts within anatomical structures, identify different levels of the spine, analyze anatomical features (e.g., vertebral disc, shape and/or size of vertebral disc, distance between adjacent vertebrae, etc.), perform spinal deformity assessment based on the analysis of anatomical features, associate the assessment with identified level of the spine, and/or provide report(s) relating to anatomical feature analyses or spinal deformity diagnoses.

In some embodiments, systems, devices, and methods described herein can implement systems, methods, and devices for spine analysis to perform anatomical feature analysis and/or to perform image analysis as further described in International Patent Application Publication No. PCT/US23/63053, filed Feb. 22, 2023, titled "SYSTEMS, DEVICES, AND METHODS FOR SPINE ANALYSIS," the disclosure of which is incorporated herein by reference, in its entirety and for all purposes.

FIG. 1 is a high-level block diagram that illustrates a system 100 for processing image data of patient anatomy and/or providing image guidance to physicians during a surgical procedure, according to some embodiments. The system 100 can include a compute device 110, an imaging device(s) 160, and, optionally, surgical navigation system(s) 170. In some embodiments, the compute device 110 can communicate with one or more imaging device(s) 160 and optionally one or more surgical navigation system(s) 170, e.g., to perform segmentation of patient anatomical structures, to perform level identification of patient anatomical structures, to perform spine analysis, to detect spinal conditions and/or other spinal deformities, and/or to provide digital guidance to surgeons during surgical procedures.

In some embodiments, the compute device 110 may be configured to perform segmentation of anatomical image data to identify anatomical parts of interest. For example, the compute device 110 can be configured to generate segmentation outputs that identify different anatomical parts of interest. Additionally or alternatively, the compute device 110 may be configured to perform level identification of different regions of the spine. The compute device 110 can be configured to generate level identification outputs, such as, for example, a level type (e.g., sacrum, thoracic, lumbar, cervical), a vertebral level (ordinal identifier), or a pair or range of vertebral levels associated with a vertebrae (and/or other nearby anatomical part(s)). Additionally or alternatively, the compute device 110 can be configured to perform anatomical feature analysis and/or spinal deformity assessment for the various identified levels. For example, the compute device 110 can be configured to analyze the anatomical parts of interest to determine spinal conditions and/or spinal deformities. In some embodiments, the compute device 110 can be configured to associate the determined spinal conditions and/or spinal deformities to one or more levels of the spine, e.g., based on the level identification outputs. In some embodiments, the compute device can be configured to generate visual representations of the patient's anatomy, and associate level identification information, anatomical feature information, and/or spinal deformity diagnoses to different parts of the patient's anatomy. In some embodiments, the compute device 110 can be configured to generate virtual representations of patient anatomy and/or surgical instruments, e.g., to provide image guides to surgeons before and/or during surgical procedures.

The compute device 110 may be implemented as a single compute device, or be implemented across multiple compute devices that are connected to each other and/or the network 150. For example, the compute device 110 may include one or more compute devices such as servers, desktop computers, laptop computers, portable devices, databases, etc. Different compute device may include component(s) that are remotely situated from other compute devices, located on premises near other compute devices, and/or integrated together with other compute devices.

In some embodiments, the compute device 110 can be located on a server that is remotely situated from one or more imaging device(s) 160 and/or surgical navigation system(s) 170. For example, an imaging device 160 and a surgical navigation system 170 can be located in a surgical operating room with a patient 180, while the compute device 110 can be located at a remote location but be operatively coupled (e.g., via network 150) to the imaging device 160 and the surgical navigation system 170. In some embodiments, the compute device 110 can be integrated into one or both of the imaging device 160 and the surgical navigation system 170. In some embodiments, system 100 includes a single device that includes the functionality of the compute device 110, one or more imaging device(s) 160, and one or more surgical navigation system(s) 170, as further described herein.

In some embodiments, the compute device 110 can be located within a hospital or medical facility. The compute device 110 can be operatively coupled to one or more databases associated with the hospital, e.g., a hospital database for storing patient information, etc. In some embodiments, the compute device 110 can be available to physicians (e.g., surgeons) for performing evaluation of patient anatomical data (including, for example, level data as described herein), visualization of patient anatomical data, diagnoses, and/or planning of surgical procedures. In some embodiments, the compute device 110 can be operatively coupled to one or more other compute devices within a hospital (e.g., a physician workstation), and can send level outputs and/or other image processing outputs to such compute devices (e.g., via network 150) for performing evaluation of patient anatomical data, visualization of patient anatomical data, diagnoses, and/or planning of surgical procedures.

Network 150 may be any type of network (e.g., a local area network (LAN), a wide area network (WAN), a virtual network, a telecommunications network) implemented as a wired network and/or wireless network and used to operatively couple compute devices, including system 100. As shown in FIG. 1, a connection may be defined between compute device 110 and any one of imaging device(s) 160, surgical navigation system(s) 170, and/or other compute devices (e.g., databases, servers, etc.). In some embodiments, the compute device 110 may communicate with imaging device(s) 160 and/or surgical navigation system(s) 170 (e.g., send data to and/or receive data from such devices) and with the network 150 via intermediate networks and/or alternate networks (not shown in FIG. 1). Such intermediate networks and/or alternate networks may be of a same type and/or a different type of network as network 150. Each of the compute device 110, imaging device(s) 160, and surgical navigation system(s) 170 may be any type of device configured to send data over the network 150 to send and/or receive data from one or more of the other devices.

In some embodiments, an imaging device 160 may refer to any device configured to image anatomical structures of a patient 180. In some embodiments, the imaging device 160 may include one or more sensors for measuring signals produced by various imaging technologies. The imaging device 160 can employ a non-invasive technology to image a patient's anatomy. Non-limiting examples of imaging devices include CT scanners, MRI scanners, X-ray devices, ultrasound devices, and combinations thereof, and the like. The image data generated by the imaging device 160 may be transmitted to any of the devices connected to network 150, including, for example, compute device 110. In some embodiments, the image data generated by the imaging device 160 can include a 2D image of an anatomical structure. In some embodiments, the image data generated by the imaging device 160 can include a plurality of 2D image scans that together provide image data for a 3D volume. The imaging device 160 can transmit the image data to the compute device 110 such that the compute device 110 can perform segmentation of the patient anatomy, perform level identification of the patient anatomy, label different anatomical parts of interest in the patient anatomy, perform spinal assessment (e.g., spinal deformity diagnosis), detect spinal conditions and/or spinal deformities, and/or associate spinal deformity diagnosis to level identification information. Optionally, the imaging device 160 can provide the image data to a surgical navigation system 170 such that the surgical navigation system can generate one or more virtual representations of the patient anatomy, e.g., for use in image-guided surgery.

The surgical navigation system 170 can be configured to provide image-guided surgery, e.g., during a surgical operation. For example, the surgical navigation system 170 may facilitate one or more of planning, visualization, and guidance during a surgical procedure. In some embodiments, the surgical navigation system 170 can include a tracking system for tracking patient anatomy, surgical tool(s), implant(s), or other objects within a surgical field. In some embodiments, the surgical navigation system 170 can include an image generator for generating one or more virtual representations of patient anatomy and/or surgical tool(s), implant(s), or other objects within a surgical field and to display these to a physician or other healthcare provider (e.g., a surgeon). In some embodiments, the surgical navigation system 170 can be configured to present a 3D display, e.g., via a 3D wearable device and/or a 3D projector or screen. In some embodiments, the surgical navigation system 170 can be configured to display a position and/or orientation of one or more surgical instrument(s) and implant(s) with respect to presurgical or intraoperative medical image data of the patient anatomy. The image data can be provided, for example, by an imaging device 160, and the surgical navigation system 170 can use the image data to generate a virtual representation of one or more anatomical parts of interest along with position and/or orientation data associated with a surgical device. Suitable examples of surgical navigation systems are described in U.S. Patent Application Publication No. 2019/0053851, published Feb. 21, 2019, and incorporated herein by reference.

Figure 2:
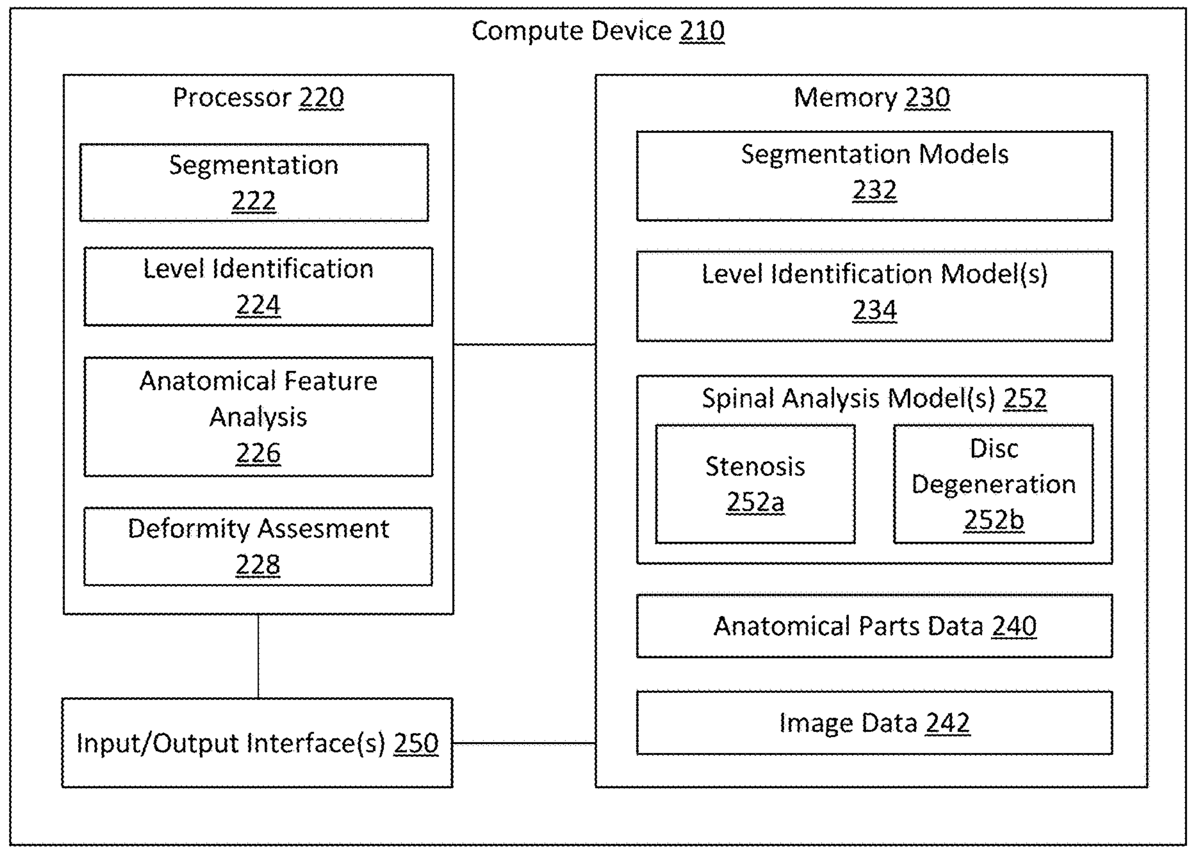
FIG. 2 schematically illustrates an example compute device for spinal deformity diagnosis and/or spinal deformity assessment, according to some embodiments.

FIG. 2 schematically illustrates an example compute device 210 for surgical planning and/or navigation, according to some embodiments. Compute device 210 can be structurally and/or functionally similar to compute device 110. While a single compute device 210 is schematically depicted, it can be appreciated that the compute device 210 can be implemented as one or more compute devices. In some embodiments, compute device 210 may be configured to segment patient anatomy, identify levels of spinal anatomy of a patient (e.g., patient 180), and/or perform anatomical feature analysis and/or spinal deformity analysis. Compute device 210 includes a processor 220, a memory 230, and one or more input/output interface(s) 250.

Memory 230 may be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, memory 230) stores instructions that cause processor 220 to execute modules, processes, and/or functions associated with segmentation 222, level identification 224, anatomical feature analysis 226, and deformity assessment 228. Memory 230 can store one or more segmentation models 232, level identification model(s) 234, spinal analysis model(s) 252 (e.g., on stenosis assessment 252*a*, on disc degeneration assessment 252*b*), anatomical parts data 240, and/or image data 242.

The segmentation models 232 can be models or algorithms for performing image-based segmentation, whereby different portions of anatomical image data can be classified or labeled. In some embodiments, the segmentation models 232 can include machine learning models, such as, for example, a CNN model, a SVM model, etc. The segmentation models 232 can be implemented by the processor 220) to perform segmentation 222. In some embodiments, the segmentation models 232 can be unique to particular anatomical regions, e.g., spinal anatomy, cardiac anatomy, etc. In some embodiments, the segmentation models 232 can be unique to particular image types, e.g., X-ray, CT, MRI, etc.

The level identification models 234 can be models or algorithms for identifying and/or labeling different levels of the vertebrae of the spine and/or other anatomical parts associated with those levels (e.g., nerves, intervertebral discs, etc.). In some embodiments, the level identification models 234 can include machine learning models, such as, for example, a CNN model, a SVM model, etc. The level identification models 234 can be implemented by the processor 220 to perform level identification 224. In some embodiments, the level identification models 234 can be unique to particular image types (e.g., X-ray, CT, MRI) and/or image views. For example, the level identification models 234 can include different models for identifying levels in axial image data, sagittal image data, and/or coronal image data. Alternatively, the level identification models 234 can include models for evaluating volumetric image data and/or combined image data, such as, for example, image data from multiple imaging systems and/or combined axial, sagittal, and/or coronal image data.

The spinal analysis model 252 can be models or algorithms for analyzing anatomical features and/or performing spinal deformity assessment or diagnoses. In some embodiments, the spinal analysis model 252 can associate spinal deformity assessment information (e.g., output of the spinal analysis model 252) with particular levels of the spine (e.g., output of the level identification models 234) and/or particular anatomical parts or structures (e.g., output of the segmentation models 232). In some embodiments, the spinal analysis model(s) 252 can include machine learning models, such as, for example, a CNN model, a SVM model, etc. The spinal analysis model(s) 252 can be implemented by the processor 220 to perform anatomical feature analysis 226 and/or deformity assessment 228. In some embodiments, the spinal analysis model(s) 252 can be unique to the type of spinal condition and/or spinal deformity being assessed. For example, the spinal analysis model(s) 252 can include a stenosis model 252*a* for stenosis assessment and/or a disc degeneration model 252*b* for disc degeneration assessment.

The anatomical parts data 240 can include information relating to anatomical parts of a patient. For example, the anatomical parts data 240 can include information identifying, characterizing, and/or quantifying different features of one or more anatomical part(s), such as, for example, a location, color, shape, geometry, or other aspect of an anatomical part. The anatomical parts data 240 can provide general or patient-specific information on different anatomical parts to enable processor 220 to perform segmentation 222, level identification 224, anatomical feature analysis 226, and/or deformity assessment 228 based on patient image data. The image data 242 can include image data associated with one or more patient(s) and/or information about different image devices, e.g., different settings of different image devices (e.g., image device(s) 160) and how those settings may impact images captured using those devices.

The processor 220 may be any suitable processing device configured to run and/or execute any of the functions described herein. In some embodiments, processor 220 may be a general purpose processor, a Field Programmable Gate Array (FPGA), an Application Specific Integrated Circuit (ASIC), a Digital Signal Processor (DSP), a Dedicated Graphics Processing Unit (GPU), and/or the like. In some embodiments, the processor 220 can be configured to perform one or more of segmentation 222, level identification 224, anatomical feature analysis 226, and/or deformity assessment 228. Segmentation 222, level identification 224, anatomical feature analysis 226, and deformity assessment 228 can be implemented as one or more programs and/or applications that are tied to hardware components (e.g., processor 220), memory 230, input/output interface(s) 250). In some embodiments, a system bus (not shown) may be configured to enable processor 220, memory 230, input/output interface(s) 250, and/or other components of the compute device 210 to communicate with each other.

While a single processor 220 that is located on a single compute device 210 is depicted in FIG. 2, it can be appreciated that processor 220 can be one or more processors that are located on the same compute device and/or different compute devices. In some embodiments, systems, devices, and methods described herein, including, for example, anatomical feature analyses and/or deformity assessments, can be implemented in a cloud platform (e.g., using one or more remote compute devices). The cloud platform can be connected to one or more databases, such as, for example, hospital databases, via a network (e.g., network 150). As such, systems, devices, and methods described herein can receive information from those databases (e.g., patient information, imaging data, etc.) and/or send information to those databases (e.g., spinal analysis reports, visualization of patient anatomy, etc.).

The input/output interface(s) 250 may include one or more components that are configured to receive inputs and send outputs to other devices (e.g., imaging device(s) 160, surgical navigation system(s) 170, etc.). In some embodiments, the input/output interface(s) 250 can include a user interface, which can include one or more components that are configured to receive input and/or present output to a user. For example, input/output interface 250 may include a display device (e.g., a display, a touch screen, etc.), an audio device (e.g., a microphone, a speaker), a keypad, and/or other interfaces for receiving information from and/or presenting information to users. In some embodiments, the input/output interface 250 can include a communications interface for communicating with other devices, and can include conventional electronics for data communication using a standard communication protocol, e.g., Wi-Fi, Bluetooth®, etc.

2. Overview of Methods

Systems, devices, and methods described herein can perform spinal deformity analyses (e.g., stenosis assessment, disc degeneration assessment, and/or other deformities assessment). In some embodiments, systems, devices, and methods can perform such analyses in combination with segmentation and/or level identification. As described above, a compute device (e.g., compute devices 110, 210) for performing segmentation, level identification, and/or spinal analysis can implement one or more algorithms or models. In some embodiments, the algorithms or models can include machine learning models, which can be trained using labeled training datasets. The machine learning models can use the training datasets to learn relationships between different features in the image data and the output spinal deformity.

In some embodiments, systems, devices, and methods described herein can perform pre-processing of image data, e.g., prior to performing segmentation, level identification, spinal feature analysis, and/or spinal deformity assessments. In many instances, image data collected using conventional imaging techniques can have low quality. For example, to avoid the risks of exposing patients to high levels of radiation, a CT imaging device may be used on a lower dose setting to capture images of patient anatomy. Similarly, MRI imaging devices using lower power may be used to capture images of patient anatomy. Such low dose or low power images can have images that have a higher amount of noise. A compute device (e.g., compute devices 110, 210) as described herein can optionally pre-process the image to remove such noise prior to performing segmentation, spinal level identification, anatomical feature analysis, and/or spinal deformity assessment.

A spinal analysis model can be used to measure or determine information about one or more anatomical features and/or to perform a spinal deformity assessment, such as described with reference to FIG. 2. In some embodiments, a spinal analysis model can be implemented as a CNN model and/or other machine learning algorithm. Put differently, a CNN model can be an example of spinal analysis model, such as for example, spinal analysis model 252 described with reference to FIG. 2. In some embodiments, the CNN model can perform anatomical feature analysis in response to receiving image data, including, for example, 2D scans and/or 3D volumetric image data of anatomical structures.

In some embodiments, systems, devices, and methods described herein can implement CNN models to obtain results from spinal image analysis. For example, CNN models can be used to perform segmentation of patient anatomical structures, to perform level identification of patient anatomical structures, to perform spine analysis, to detect spinal conditions and/or other spinal deformities, generate quantitative data series to be visualized by registering to image data as disclosed herein, and/or to provide digital guidance to surgeons during surgical procedures. Further details of CNN models configured for performing segmentation are described in U.S. Patent Application Publication No. 2019/0105009, U.S. Patent Application Publication No. 2020/0151507, U.S. Patent Application Publication No. 2020/0410687, U.S. Provisional Patent Application No. 63/187,777, and PCT Patent Application No. PCT/US22/29000, incorporated above by reference. Further details of CNN models configured for performing level identification are described in U.S. Patent Publication No. 2020/0327721 and U.S. Provisional Patent Application No. 63/256,306, incorporated above by reference.

In some embodiments, the CNN model can be configured to receive and/or extract from image data information relating to a region of interest (e.g., parameters, characteristics, or other information of anatomical features such as vertebrae, intervertebral disc, intervertebral foramen, nerves, etc.). For example, the CNN model can be configured to receive or extract information including shape of an anatomical feature, surface area of an anatomical feature, distance between two adjacent anatomical features, a combination thereof, and/or the like. The CNN model can be configured to classify one or more anatomical parts and/or structures based at least in part on the analysis of the anatomical feature information (e.g., shape, surface area, distance, etc.). In some embodiments, the CNN model can be configured to assess a state or condition of one or more anatomical parts and/or structures based on the anatomical feature information. For example, the CNN can be configured to classify one or more vertebral levels as having mild spinal deformity, medium spinal deformity, severe spinal deformity, no spinal deformity, etc. based on the anatomical feature information.

In some embodiments, one or more models for performing segmentation, level identification, and/or spinal analysis can be used together, e.g., in a model or algorithm that combines multiple such processes (segmentation, level identification, and/or spinal analysis) together. For example, in some embodiments, a model can be configured to receive image data, to perform segmentation on that image data, to identify different levels of vertebrae in the image data, to perform analysis of different spinal deformities, and to output information on one or more anatomical parts and/or structures.

Machine learning, for example (e.g., using models) can process medical images and create structured datasets that quantify certain structures, parameters, and biomarkers. In some implementations, such structured datasets can include non-image based, quantitative and/or qualitative structure data that can be valuable for analysis of a patients care pathway and treatment. Structured datasets, including non-image data, are not easily usable by surgeons and radiologists for image interpretation, as they are normally formatted for machine reading in formats such as CSV or JSON. Thus, there is a need to be able to provide the valuable information from structured datasets, including non-image data, that machine learning generates in a way that is integrated with a user's existing workflow so that efficiency is gained instead of lost through the use of this new information.

Moreover, often healthcare providers (e.g., primary care physicians, surgeons) can be better equipped to manage the patient's overall health and care and may benefit from additional understanding of their patient's medical imaging results. In some instances, however, such health care providers may not be trained to interpret medical imaging data and may have difficulty providing adequate guidance, referrals, and/or recommendations to their patients due to reliance on image interpretation performed by radiologists. These image interpretations, including structured datasets with non-image based, quantitative and/or qualitative structure data can provide valuable insights into patient care. But the image interpretations and non-image-based data not standard in format and have significant variance between radiologists. Thus, there is a need to be able to provide the valuable information from structured datasets, in a manner readable by healthcare providers using conventional or preexisting data visualization methods without having to resort to complex equipment to read complex data in non-standard formats.

Figure 3:
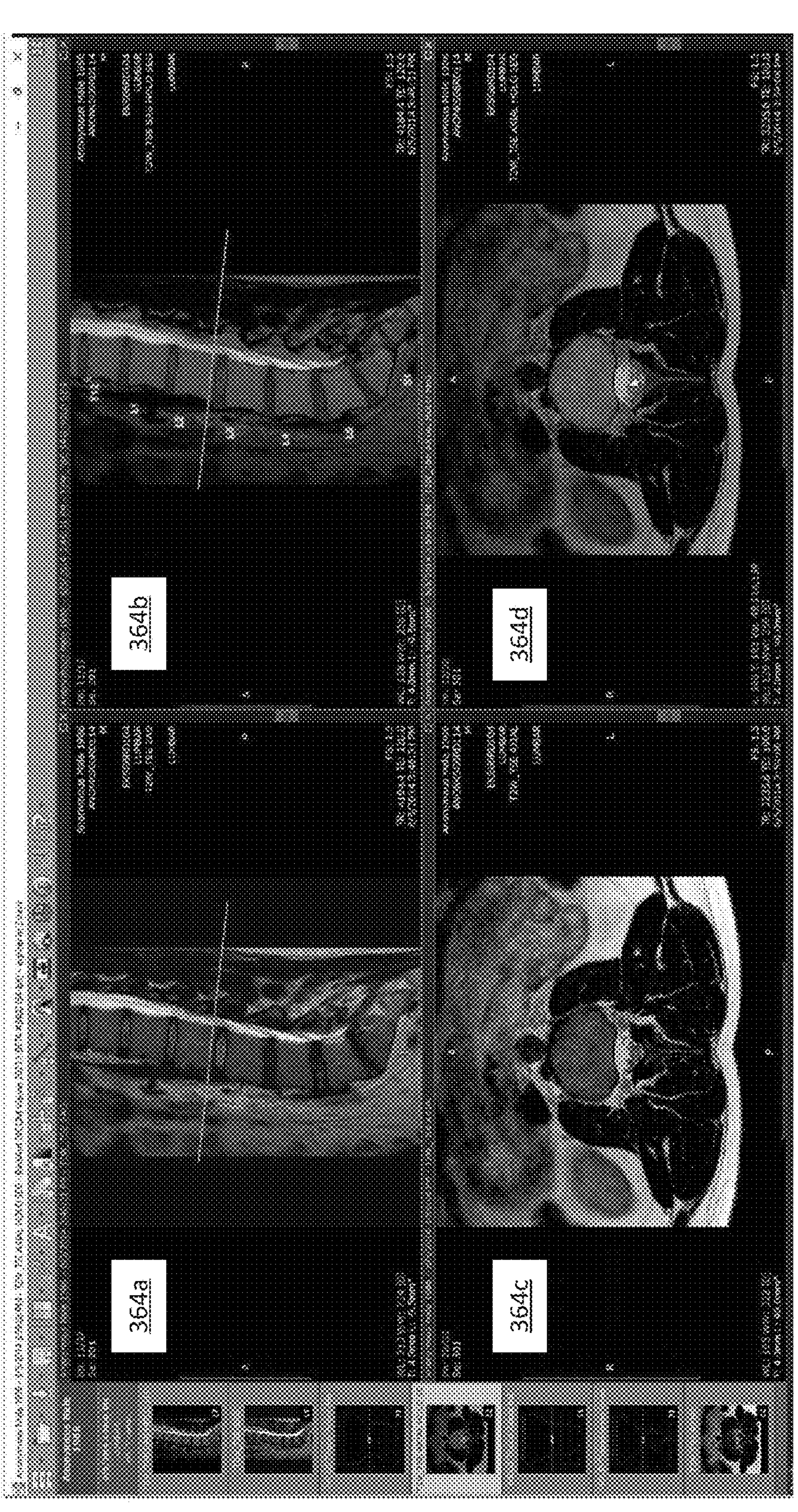
FIG. 3 is a schematic illustrating a data visualization interface, according to some embodiments.
Figure 4:
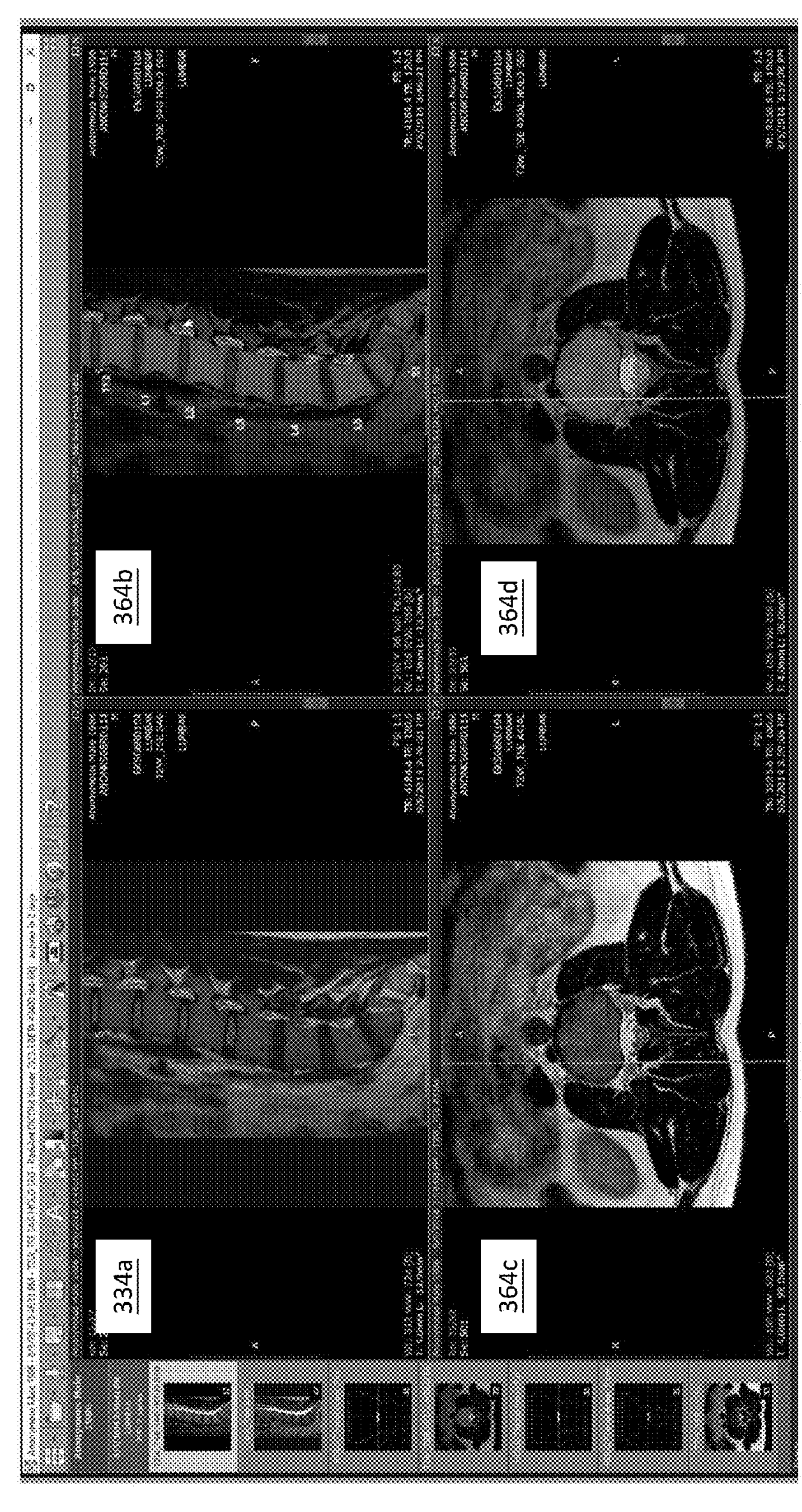
FIG. 4 is a schematic illustrating a data visualization interface, according to some embodiments.

One method of image visualization used by surgeons, radiologists, readers, or other users interpreting imaging data involves loading DICOM series into a DICOM viewer and scrolling through the image series to view the patient's anatomy. FIGS. 3 and 4 show an example data visualization interface (also referred to as "interface" herein) 362 a DICOM viewer. The interface includes multiple panels 364*a-d*. Each panel can be configured to visualize image data from a series that can include image data acquired along an anatomical plane (e.g., axial, or sagittal). The interface can visualize both a sagittal image (e.g., in panel 364*a*) and an axial image (e.g., in 364*c*) corresponding to an anatomical point of interest in a patient. The interface can be configured to simultaneously visualize image data from a complementary series (e.g., a series of images including image segmentation results) along one a sagittal image (e.g., in panel 364*b*) and an axial image (e.g., in 364*d*) corresponding to the same anatomical point of interest in the patient. When a user scrolls through images along an identified plane (e.g., sagittal plane) the panel showing an image along the other plane (e.g., axial plane) includes a marker indicating the position of the currently viewed sagittal slice. The data visualization interface 362 can be configured such that scrolling through the data series through images along the identified axis results in the marker indicated in the panel showing image data in the other axis to move as it updates the position of the currently viewed slice in the other axis. For example, scrolling through axial images from top to bottom in panels 364*c* and 364*d* induces the marker in panels 364*a* and 36*b* to updated in position from top to bottom.

As described herein, one method to visualize non-image (quantitative and/or qualitative) data can include creating several additional data series based on the image data, for example, additional DICOM series for DICOM data. The additional data series are defined to include and/or represent the non-image data, and are appended to the original image data, for example the original DICOM study. In some example implementations, the systems and methods disclosed can be used to obtain non-image quantitative for example via machine learning. In some implementations, the non-image quantitative data can be aggregated into a data series that is configured to be visualized through a data visualization interface (e.g., DICOM viewer). The data series can be transformed into a structured that can be registered and/or mapped to a series of image data. For example, the structured data can include values where each value corresponds to a slice of image in the image data series. The data series and the structured data can be used to generate a graph where one of the axes of the graph (e.g., the y-axis) represents the individual slices within the DICOM series, and the other axis (e.g., X-axis) represents a feature or measure that the quantitative data represents (e.g., an area, a volume, a distance measure, etc.). The graph can be presented in any suitable panel in the data visualization interface (e.g., DICOM viewer) and include any suitable annotation or label indicating information about the data series and/or structured data. In some implementations, the graph can include a marker indicating the position of the currently viewed slice in the image data series. This data visualization can be implemented for slices acquired along the axial plane or sagittal plane. In some implementations, the data series in the structured data can be co-registered with the rest of the image data in the DICOM study data so that when the image data is viewed in a DICOM viewer and the images are scrolled through (for example a user scrolling through the axial cuts of an MRI), the graph is updated accordingly to show information corresponding to the currently viewed slice in the other panels of the data visualization interface. That is the graph can be updated to indicate a movement in the marker in a synchronized manner with the change in the slice viewed (e.g., as a user scrolls through axial slices, a marker in a graph showing a quantitative data series moves along the y-axis representing the axial slices). Said in another way, as a user scrolls through images, the graph DICOM scrolls, it is configured in such a manner that it will display a marker that identifies the information that is relevant to the particular slice being viewed.

Figure 5:
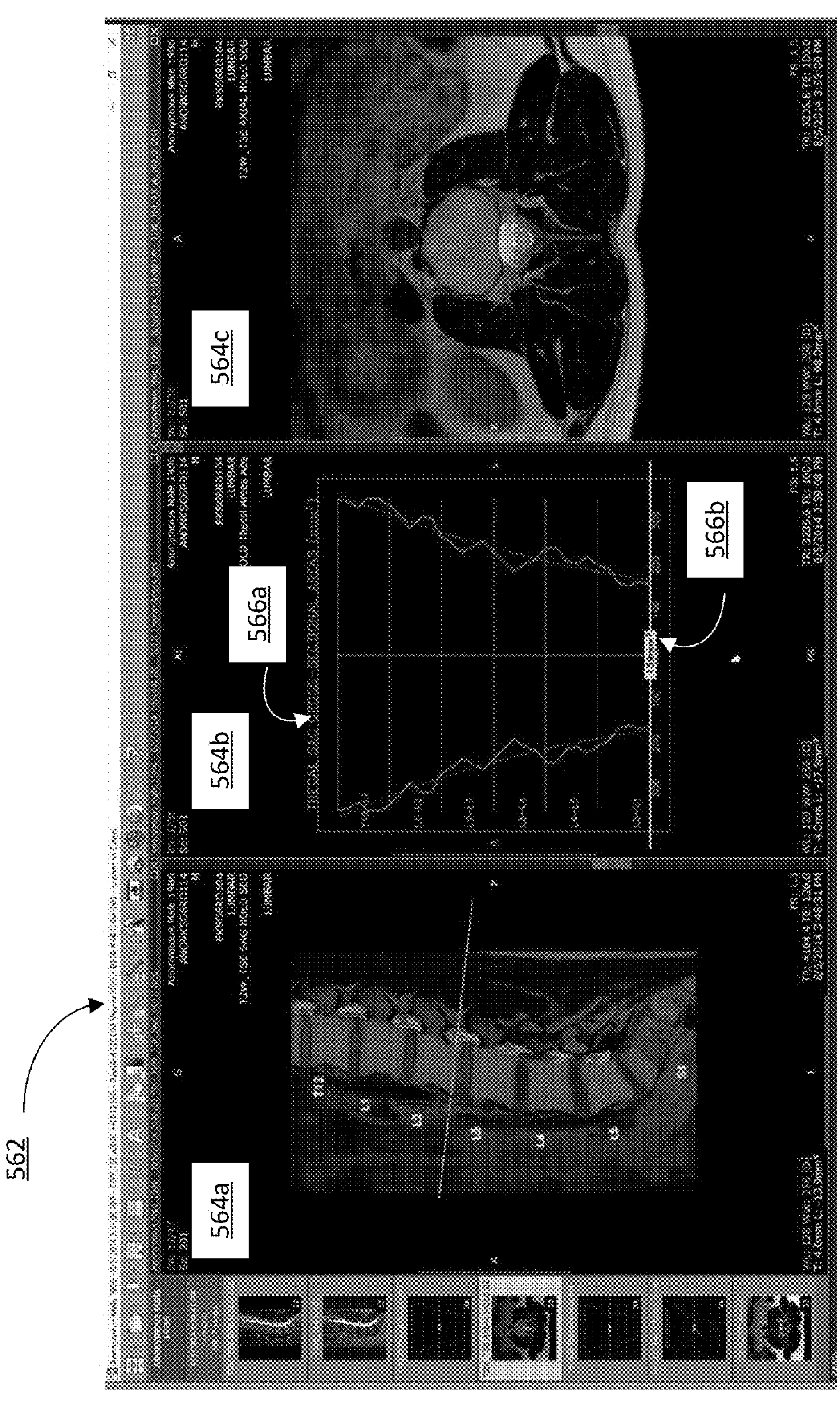
FIG. 5 is a is a schematic illustrating a data visualization interface, including a visualization of a data series representing non-image data, according to some embodiments.
Figure 6:
FIGS. 6-15 are schematics illustrating a data visualization interface including a visualization of a data series representing quantitative data registered to imaging data, according to some embodiments.
Figure 7:
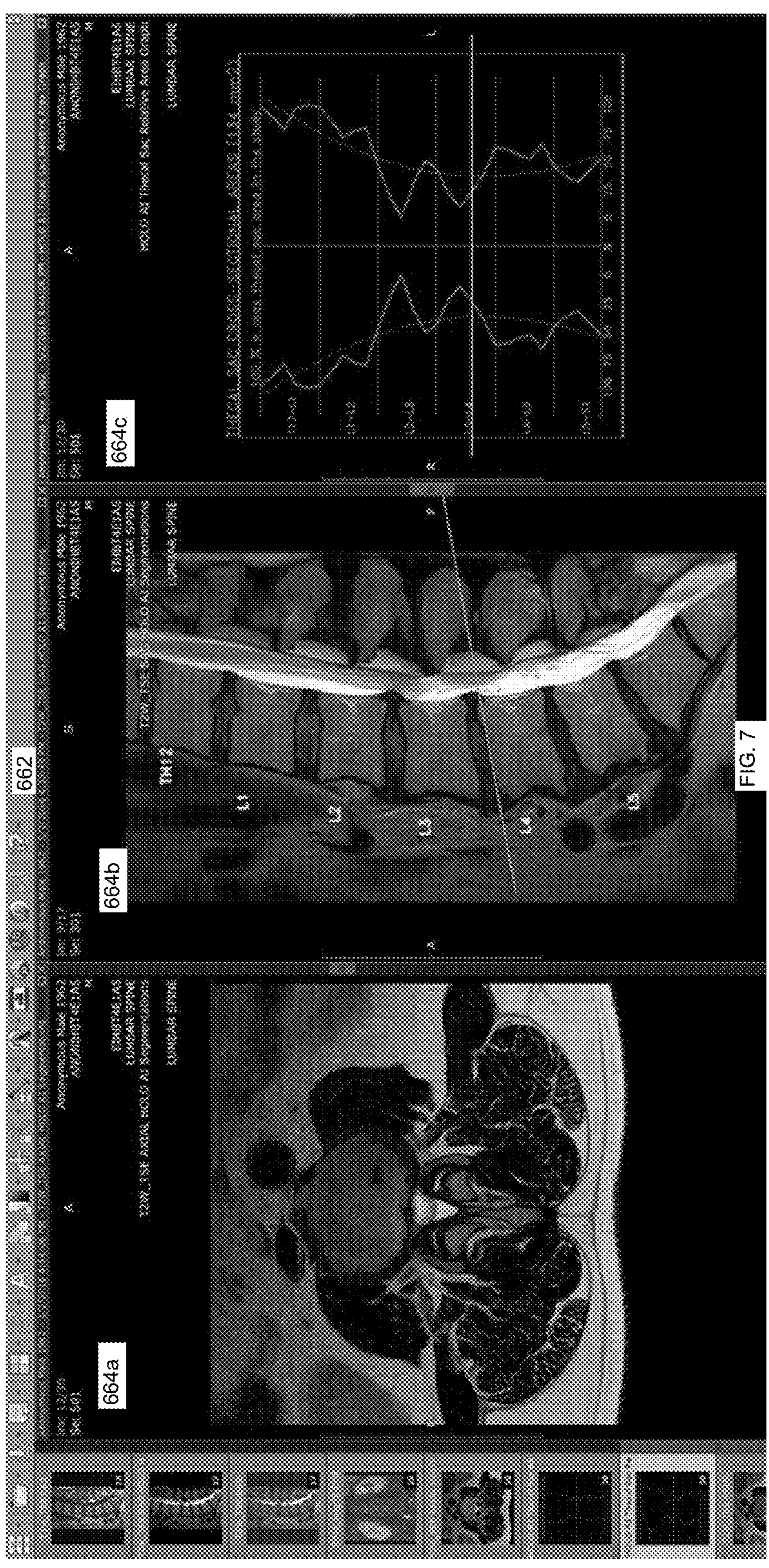
Figure 8:
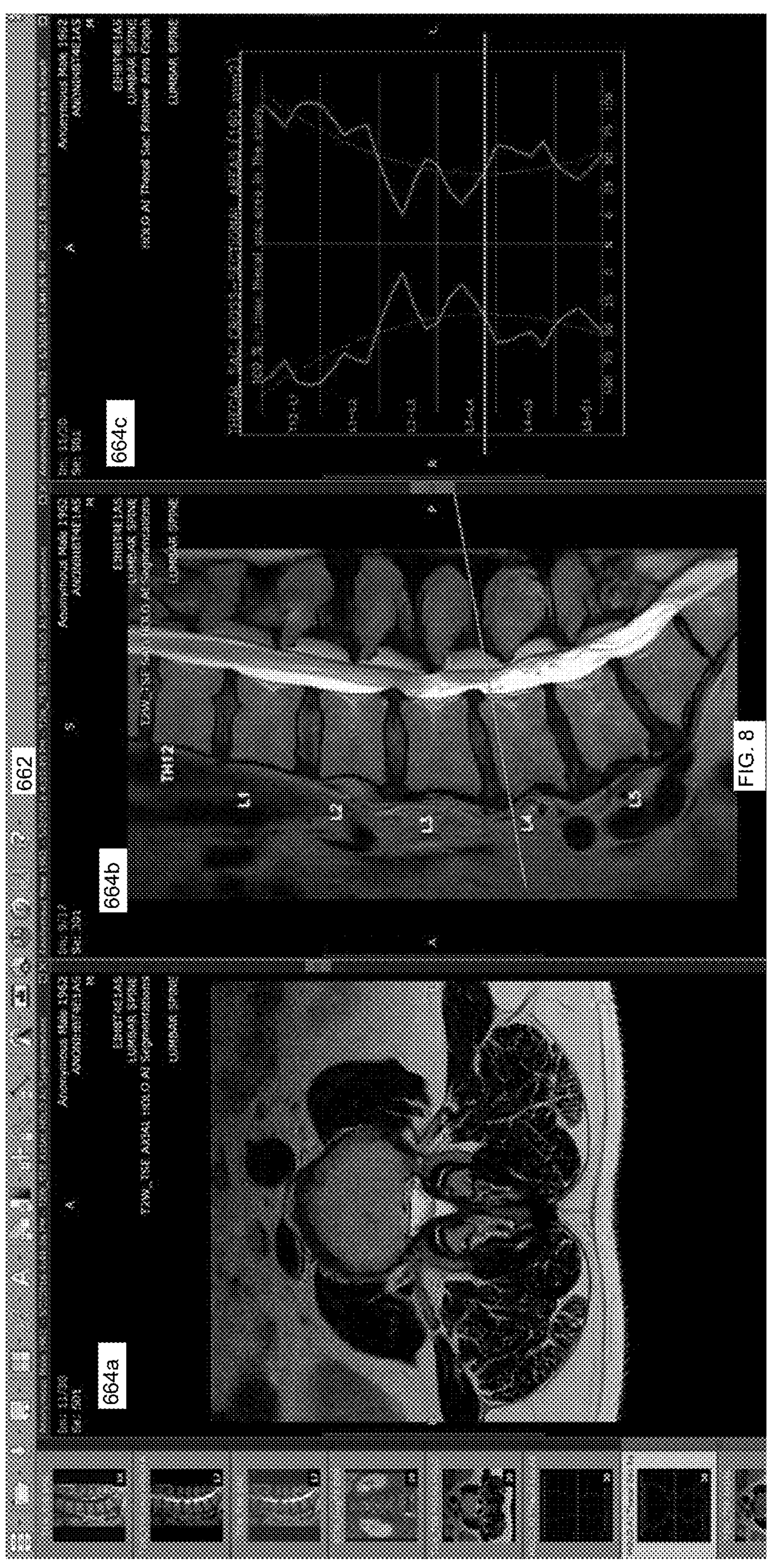
Figure 9:
Figure 10:
Figure 11:
Figure 12:
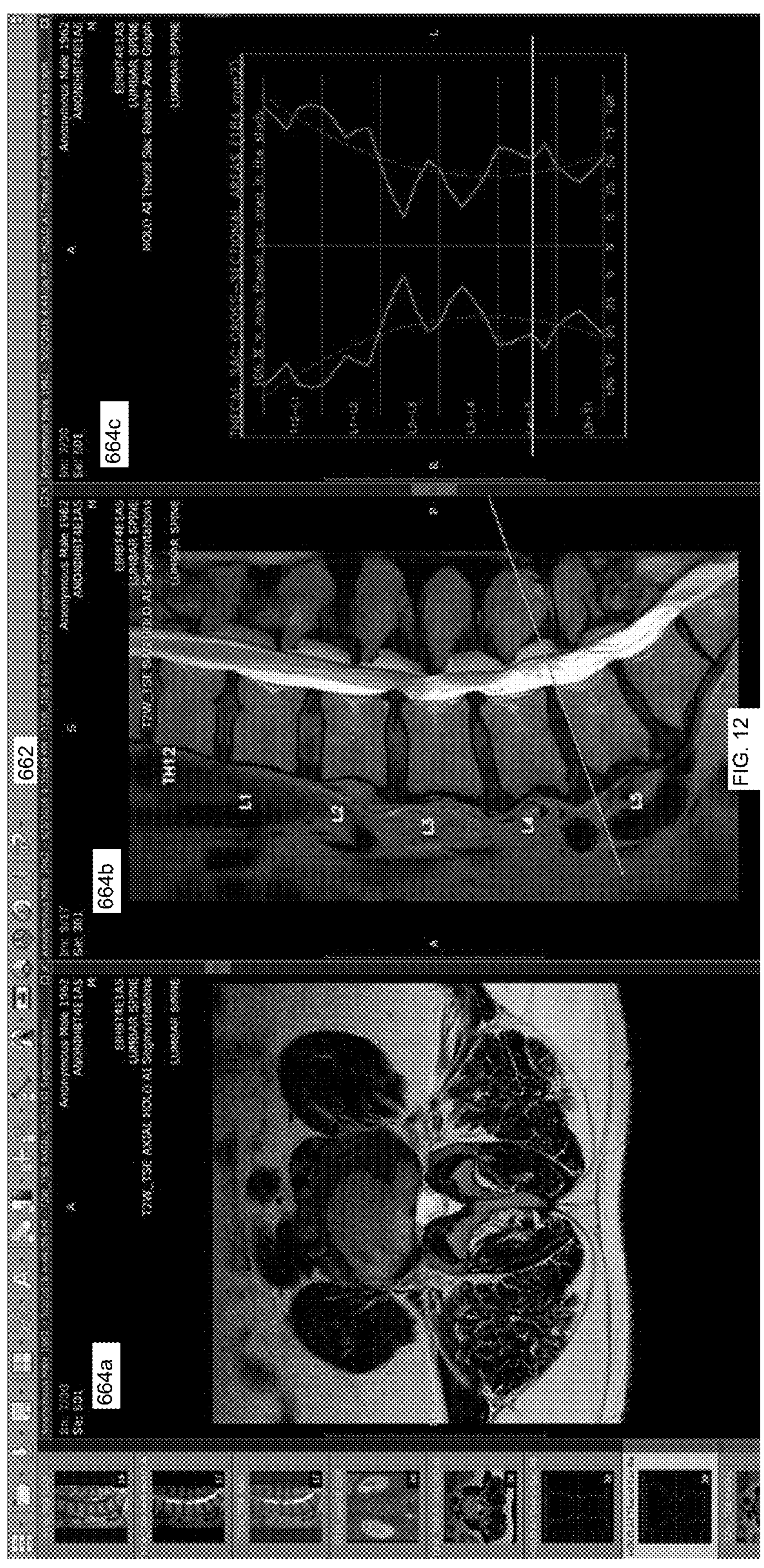
Figure 13:
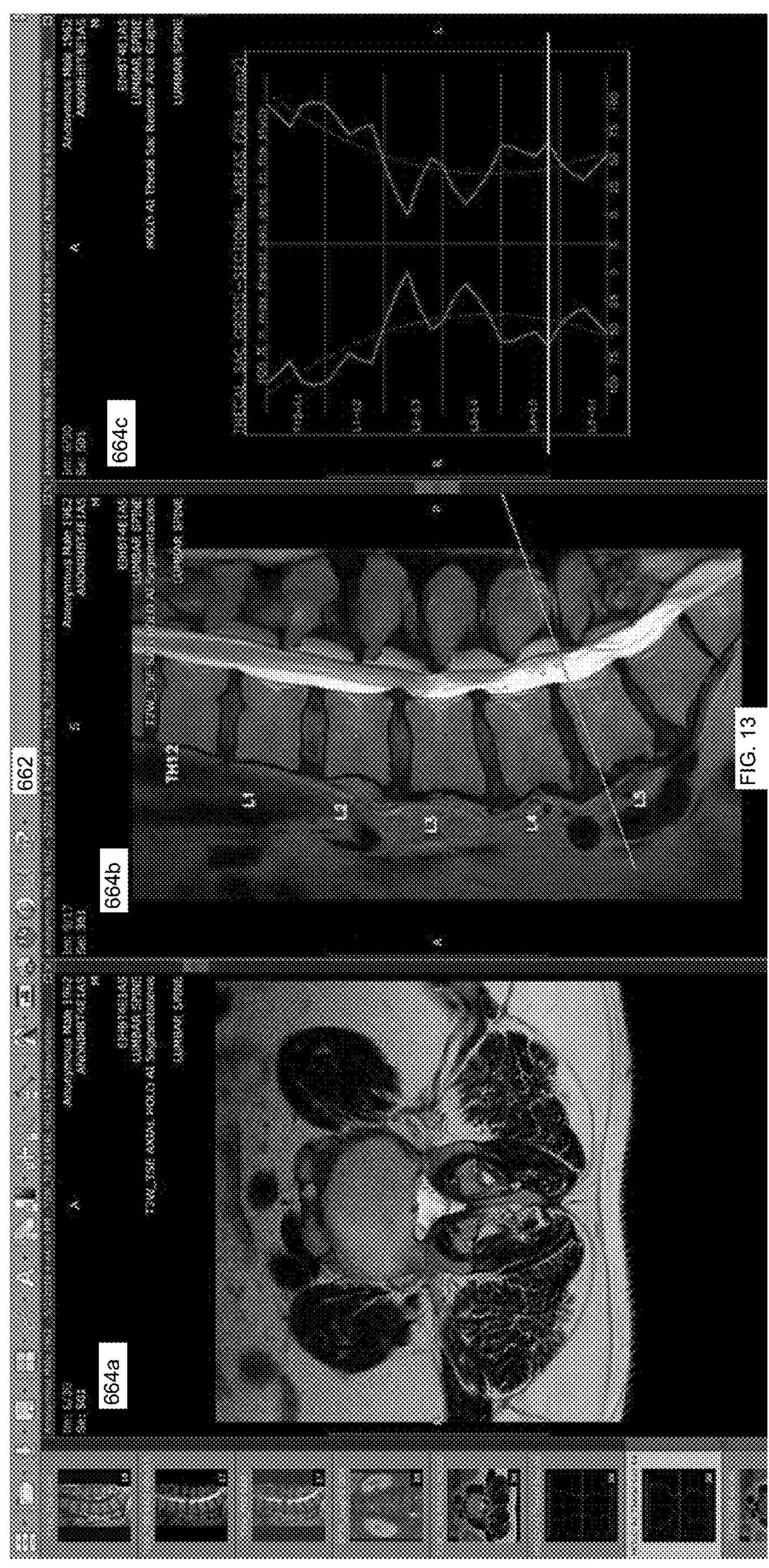
Figure 14:
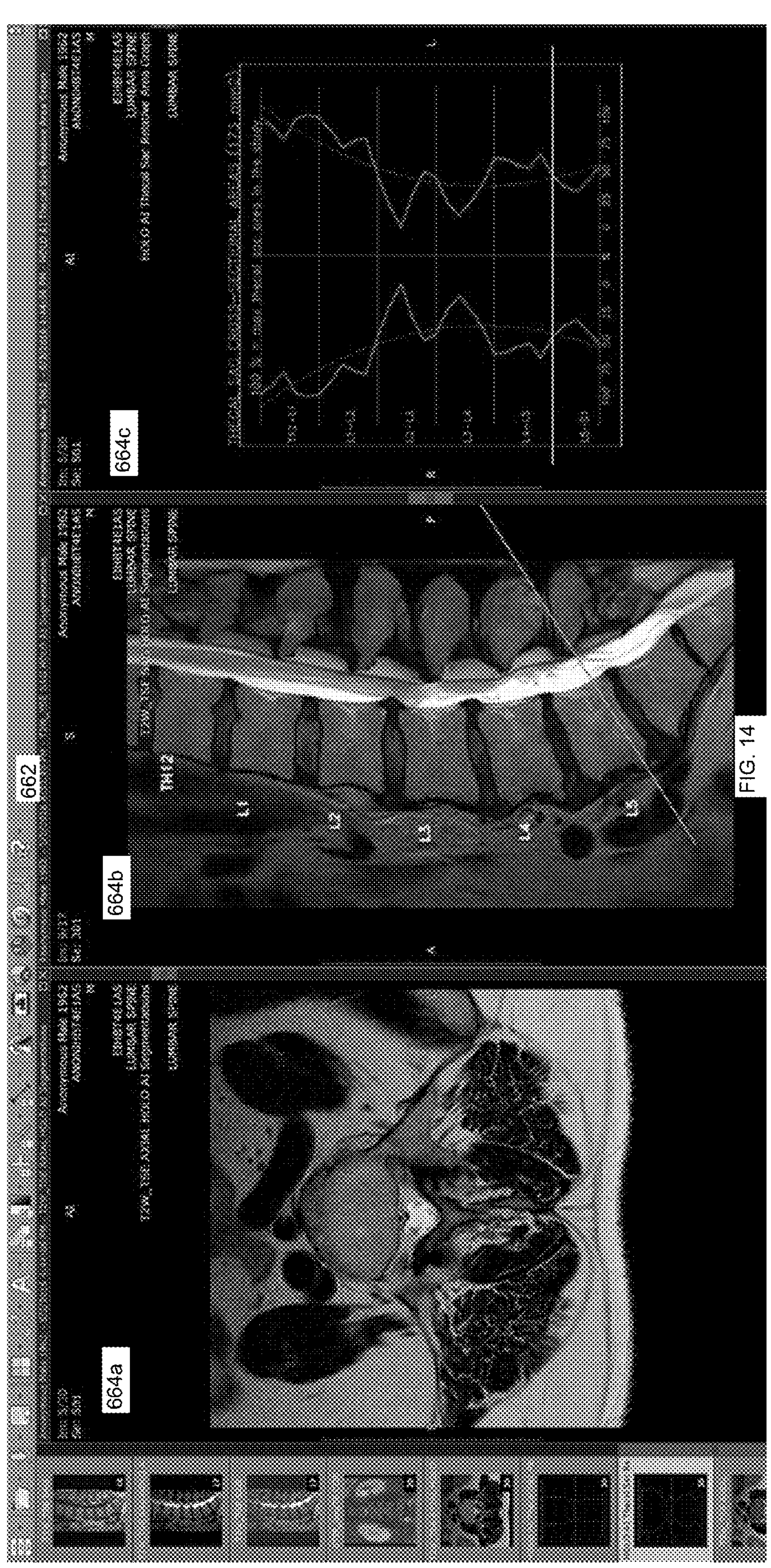
Figure 15:
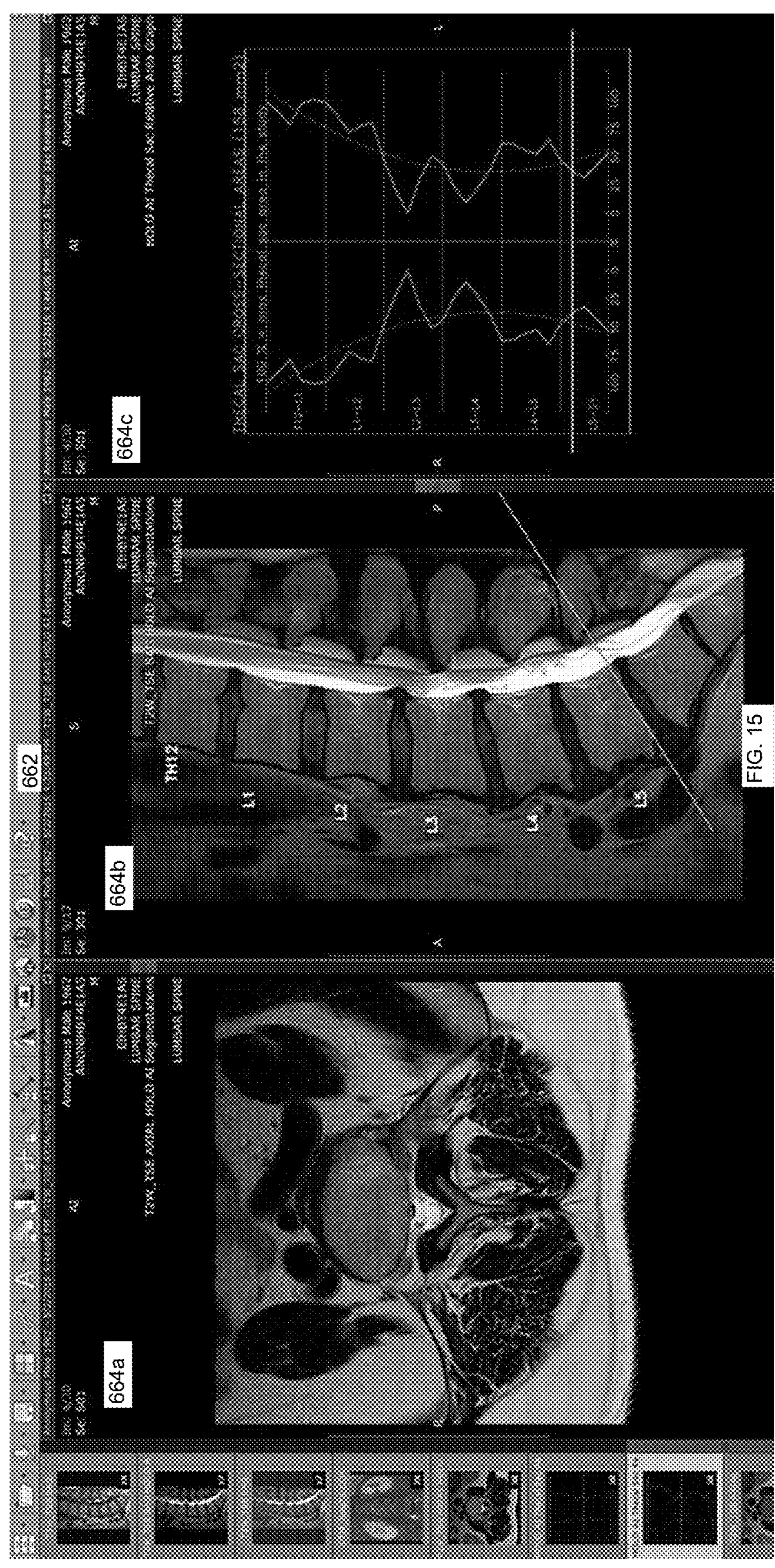

FIG. 5 shows an example illustration of a data visualization interface 562, including a visualization of a data series representing non-image data, according to some embodiments. The interface 562 includes panels 564*a* and 56*c* showing image data, and panel 564*b* showing non-image data which is a quantitative data series represented in the form of a graph 566*a*. The graph 566*a* has a marker 566*b* indicating the position of the currently viewed axial image, along the spinal column.

FIGS. 6-15 are schematics illustrating a data visualization interface 662 including a visualization of a data series representing quantitative data registered to imaging data, according to some embodiments.

The interface 662 includes panels 664*a* and 664*b* showing axial and sagittal images both also showing segmentation results. Panel 664*a* shows an axial image taken at an identified position along the patients spina column, and that position of that axial image in panel 664*a* along the spinal column is indicated in the sagittal image in panel 664*b*. The interface 662 includes panel 664*c* showing a graph depicting structured data that is quantitative non-image information related to the axial image shown in panel 664*a* at the position shown in panel 664*b*. The graph in panel 664*c* shows data series representing thecal sac cross-sectional area corresponding to the axial image shown in panel 664*a* at the position indicated in panel 664*b*. The position of the axial image shown in panel 664*a* moves from a relatively rostral position in FIG. 6 to increasingly caudal position in FIGS. 7-15. With each change in axial image position, the marker in panel 664*b* indicates the position of the axial image in the rostro-caudal axis, and the marker in the graph in panel 664*c* shows the position on the graph along the y-axis, indicating the data point corresponding to that axial image location. The value of the data point is indicated along the x-axis (i.e., thecal sac area in that axial image along the rostro-caudal axis of the patient).

The disclosed method and system of visualization of non-image data series in a synchronized manner with image data series in a data visualization interface configured for viewing image data series achieves the dual aim of providing a high-level summary of the quantified information (the whole graph that shows the results from all the slices) as well as providing the individual measurement when it is relevant to see it as the user is viewing a particular slice.

The data visualization disclosed herein presents an intuitive representation of the data that is easily comprehensible for users who may be untrained to interpret radiological imaging data. The format of structured data disclosed herein has a unique formulation in that the graphed data reflects the real anatomic layout of the structures for which the information is provided. The left-hand side of the graph provides information on the level that is of interest. The graphic data provides either an intuitive picture of the particular structure for each slice of the DICOM dataset (thecal sac, subarticular space and foraminal) or a summary of the structure volume for that particular level. For the data presented as a cross sectional area for each slice, the data is formatted to resemble the spinal canal. It is graphed top to bottom and it is visually indicated in an easily comprehensible manner such that narrowing of the structure is toward the middle of the graph, whether it is right or left sided. Because 'stenosis' is narrowing, the graph narrows in areas that are more demonstrated to have stenosis. For the data presented as volumes per level, the data is formatted to resemble the volume of that structure that is measured. If there is a left/right distinction for that structure it is separated out and shown such that it reflects what is shown in the actual imaging and real anatomy. Structures that have more of less volume are visually easy to detect and conclusions can be drawn by looking at a particular level and comparing the volumes of several structures at that level.

In use, a surgical navigation system (e.g., the surgical navigation system 170 of system 100 shown in FIG. 1) can be used to generate a structured data. The structured data can be generated for any image data (e.g., DICOM data) and configured to be readable and visualized using a data visualization interface (e.g., DICOM viewer) configured to visualize the image data (DICOM image data). To generate the structured data, a subset of the reference imaging metadata (e.g., DICOM tags from the images and series in a DICOM imaging study) is extracted from the reference imaging data and applied to a new dataset (ex: a HOLO DICOM series). This allows the new dataset to be compatible with the reference imaging data and supported by the same tools normally used for viewing the reference images (ex: DICOM viewers, Picture Archiving and Communications System (PACS) viewers, Electronic Health Record (EHR) viewers, and/or the like). The new dataset can be grouped and appended in these tools to the original imaging data (e.g., categorized and viewable as an additional imaging series within the reference imaging study).

The visual elements of the analysis (e.g., graphs, values, labels) are then transformed relative to the reference imaging metadata and added to the new dataset (e.g., as DICOM pixel arrays) so that the visual elements of the analysis are correlated with the reference images (e.g., axes of graphs are scaled and oriented to the match the positional values of the reference imaging metadata). This results in visual analysis elements that are accurately displayed and synchronized relative to the reference imaging.

Figures 16A, 16B, 16C:
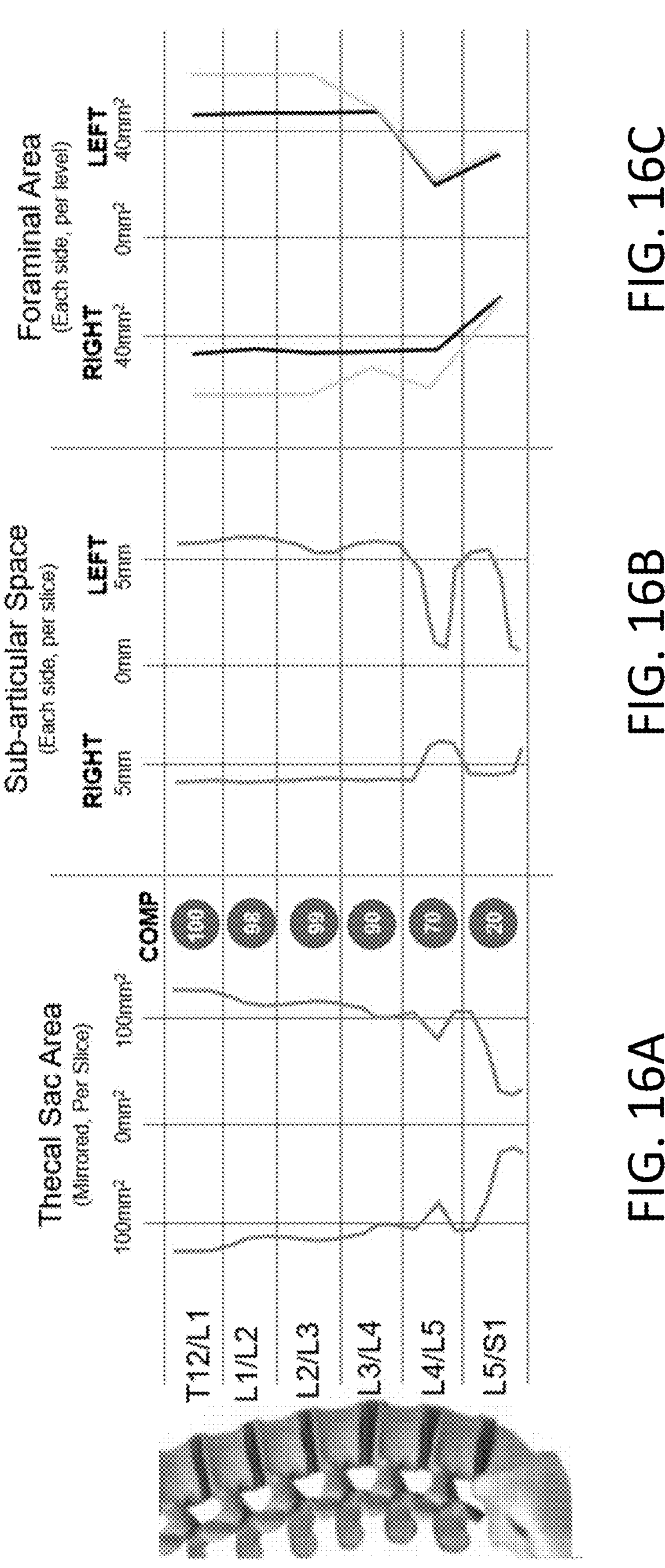
FIGS. 16A-16C are example plots showing visualization of a data series representing quantitative data, according to some embodiments.
Figures 17A, 17B, 17C:
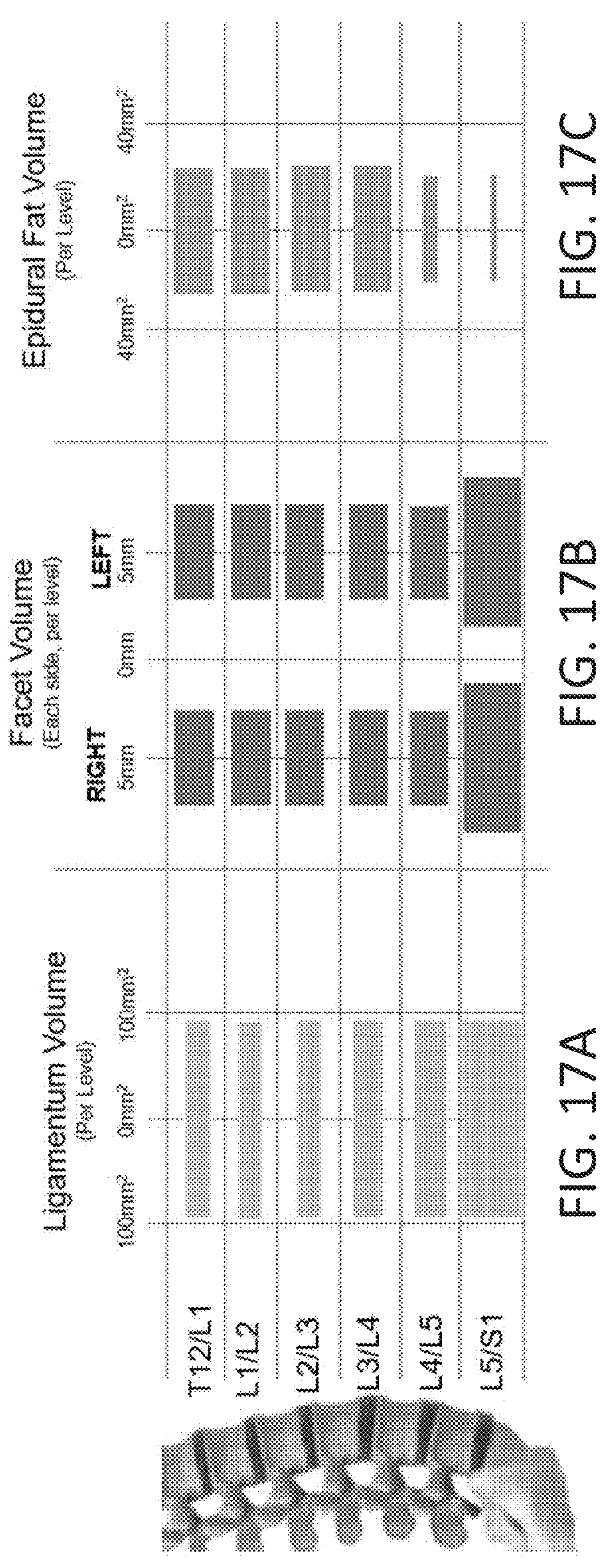
FIGS. 17A-17C are example plots showing visualization of a data series representing quantitative data, according to some embodiments.
Figures 18A, 18B, 18C:
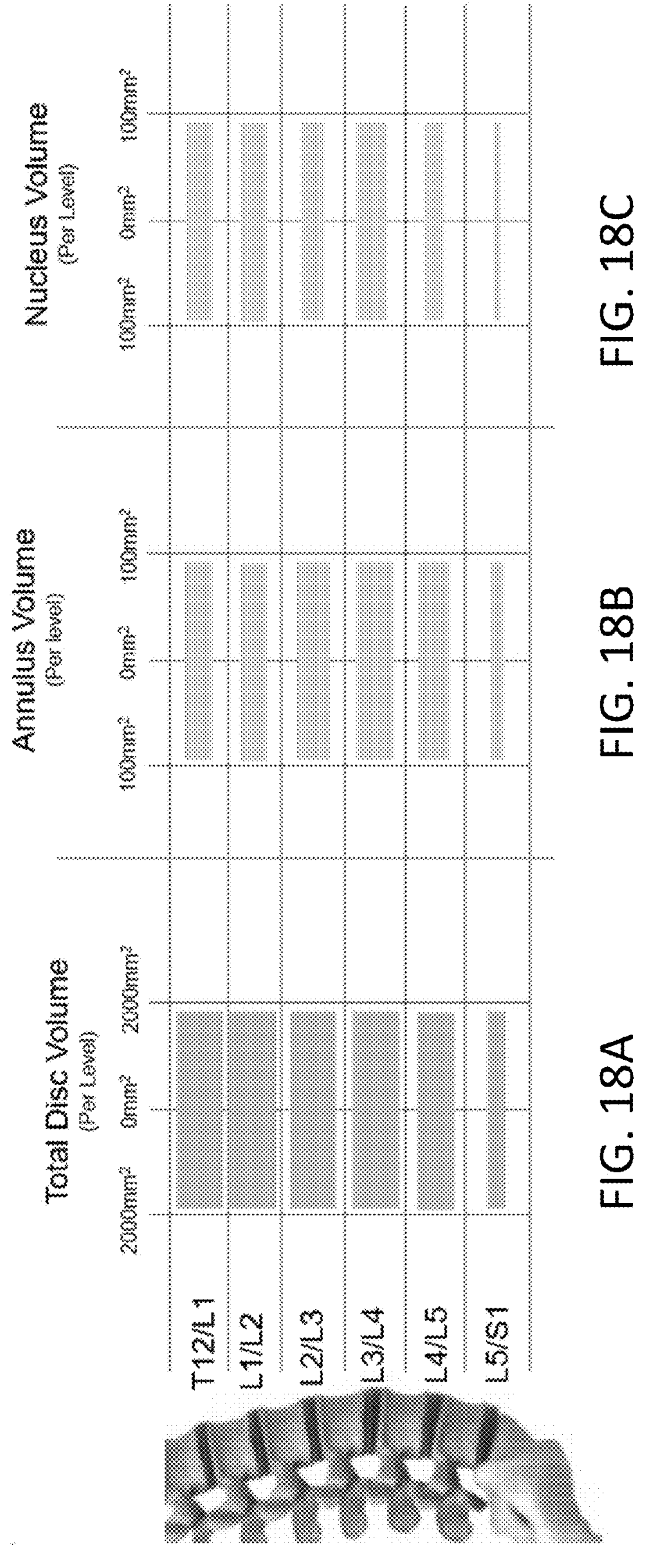
FIGS. 18A-18C are example plots showing visualization of a data series representing quantitative data, according to some embodiments.
Figure 19:
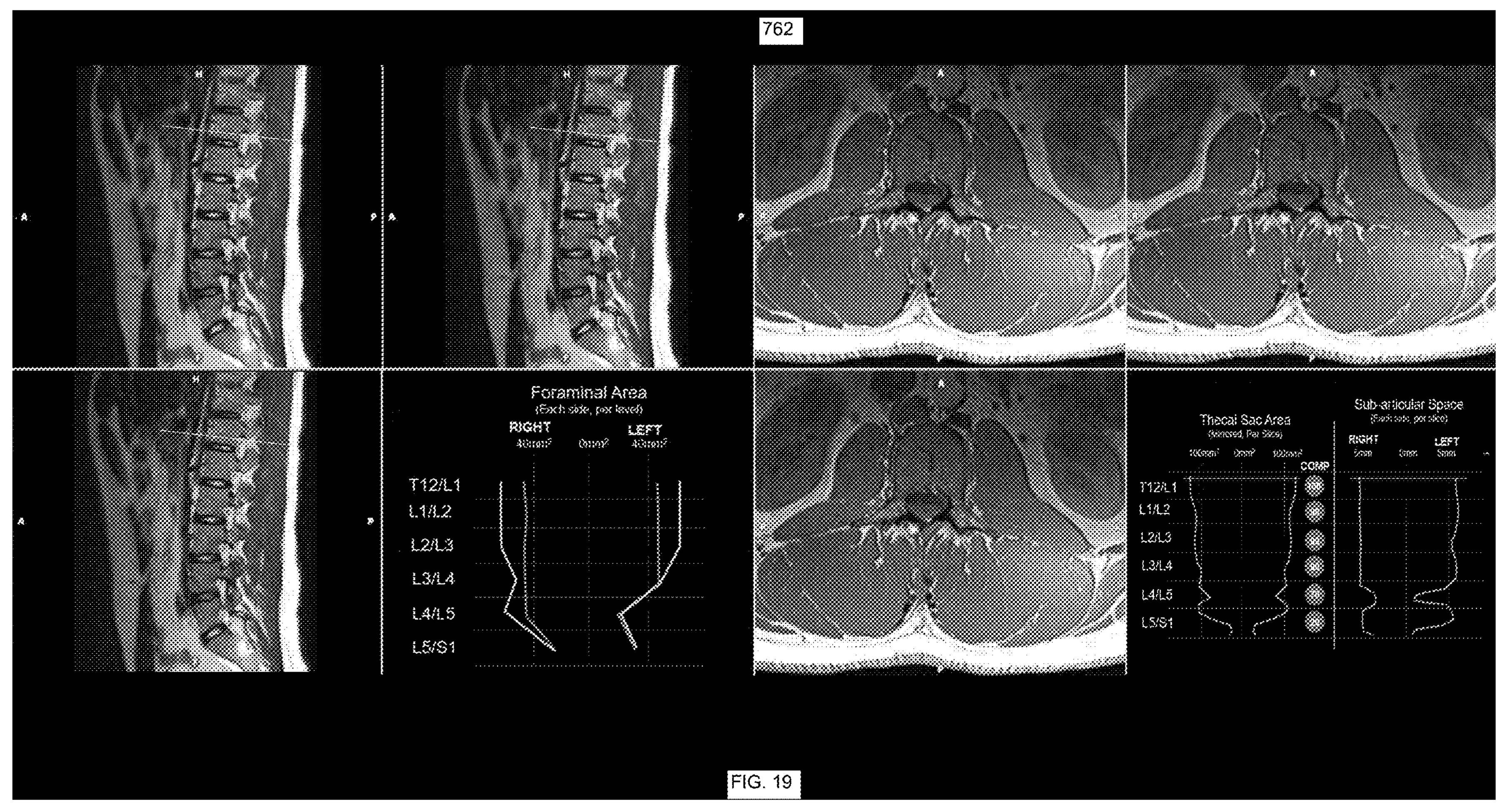
FIGS. 19-36 are schematics illustrating a data visualization interface including a visualization of a data series representing quantitative data registered to imaging data, according to some embodiments.
Figure 20:
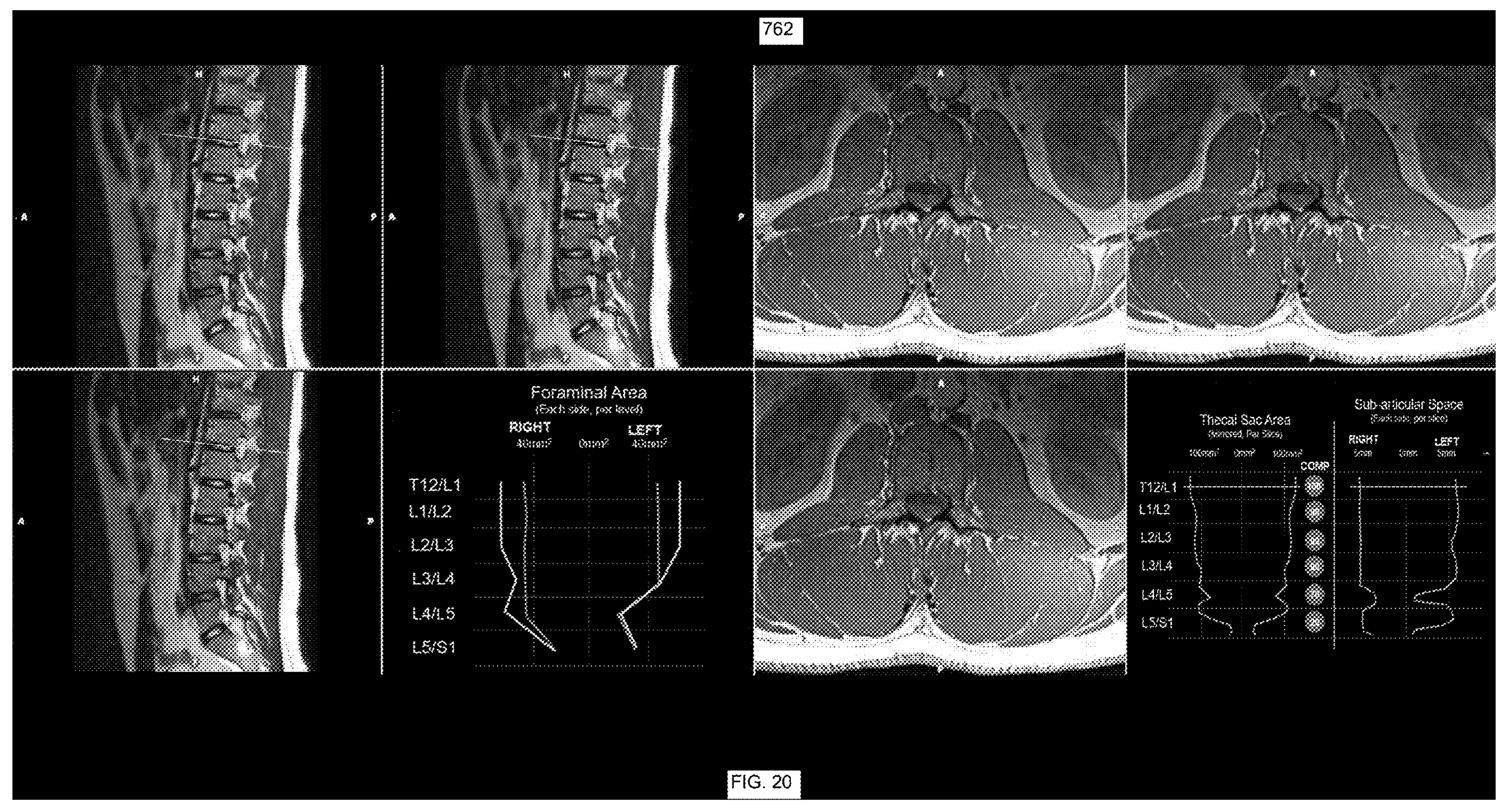
Figure 21:
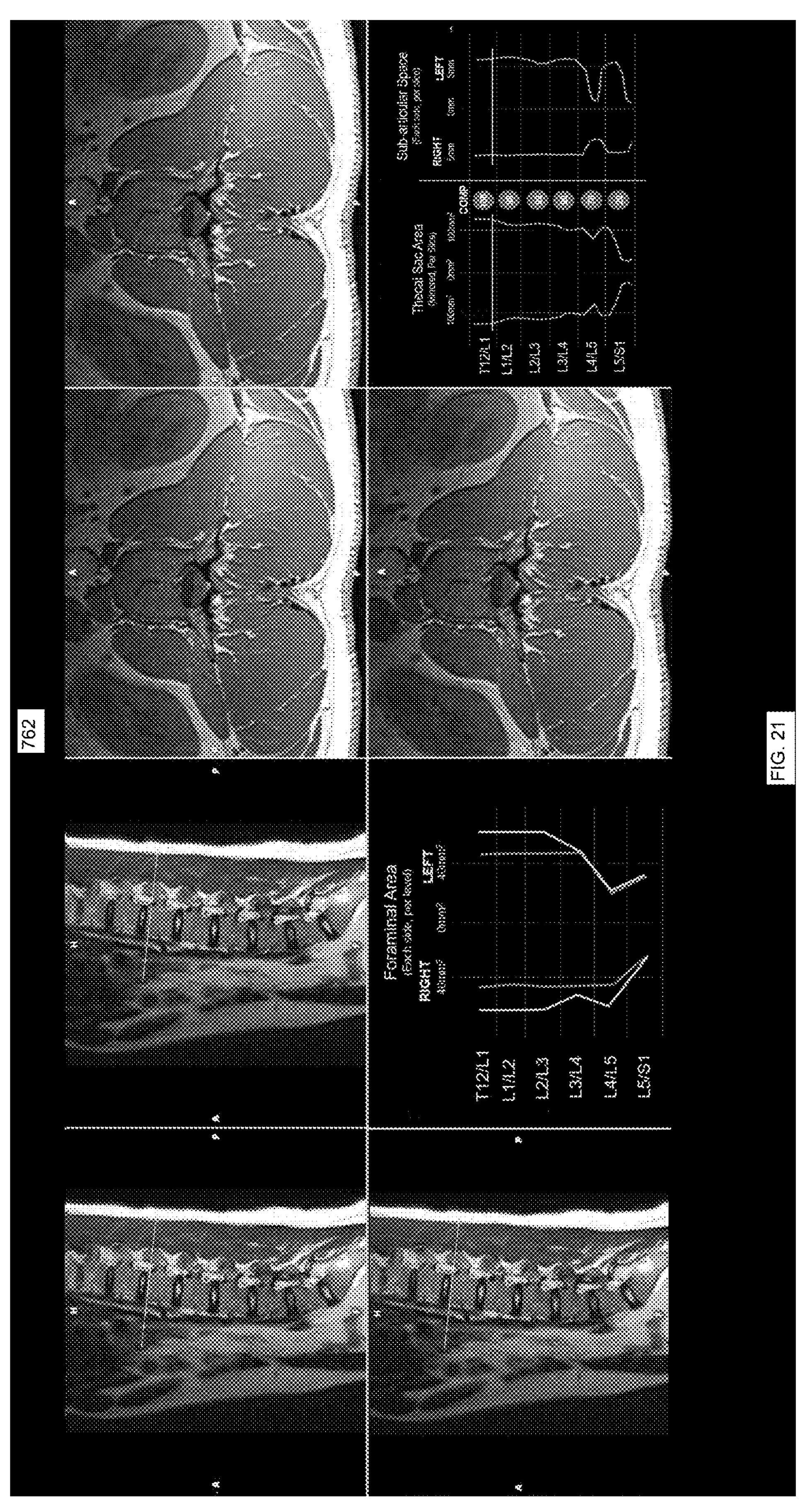
Figure 22:
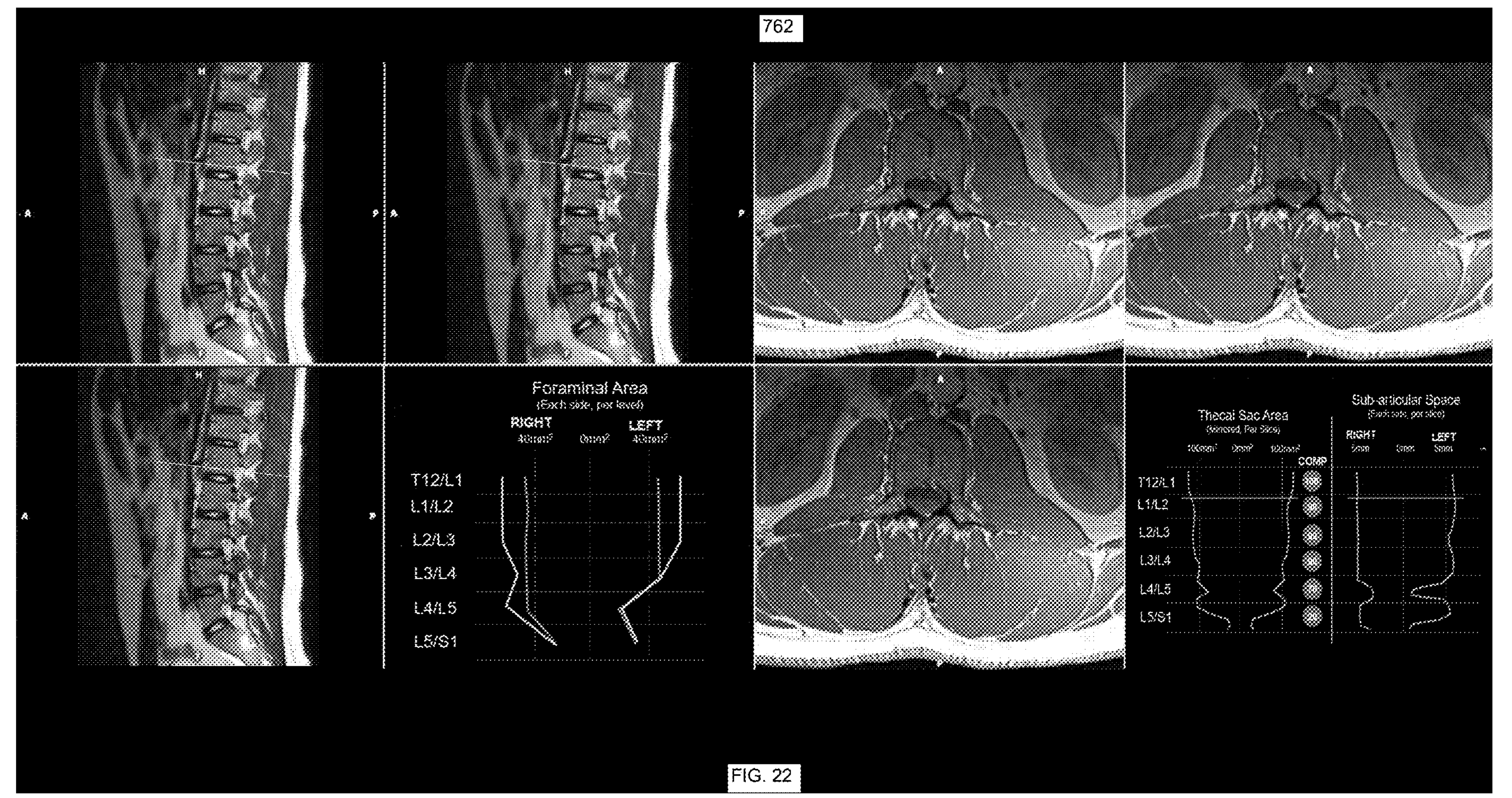
Figure 23:
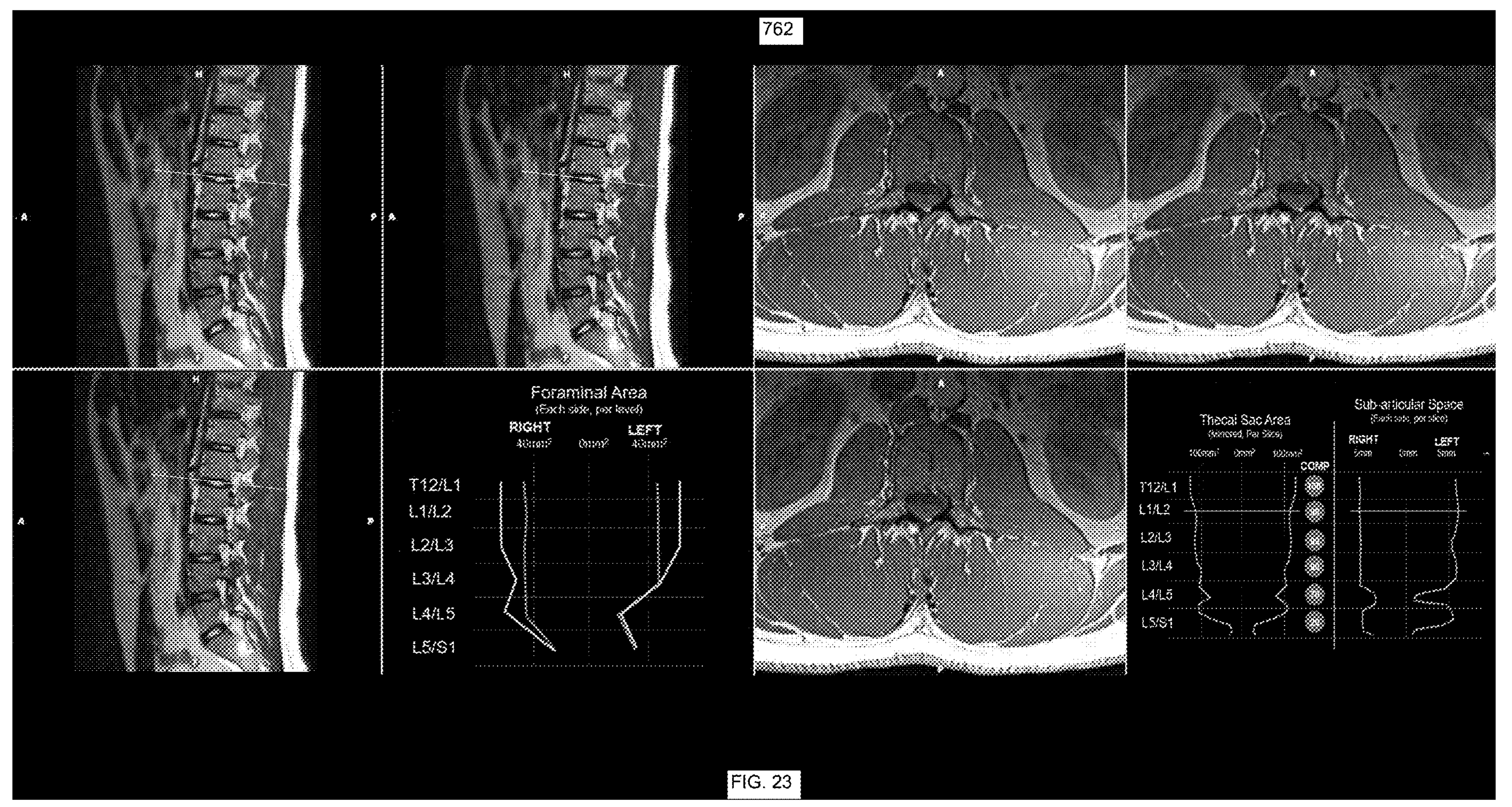
Figure 24:
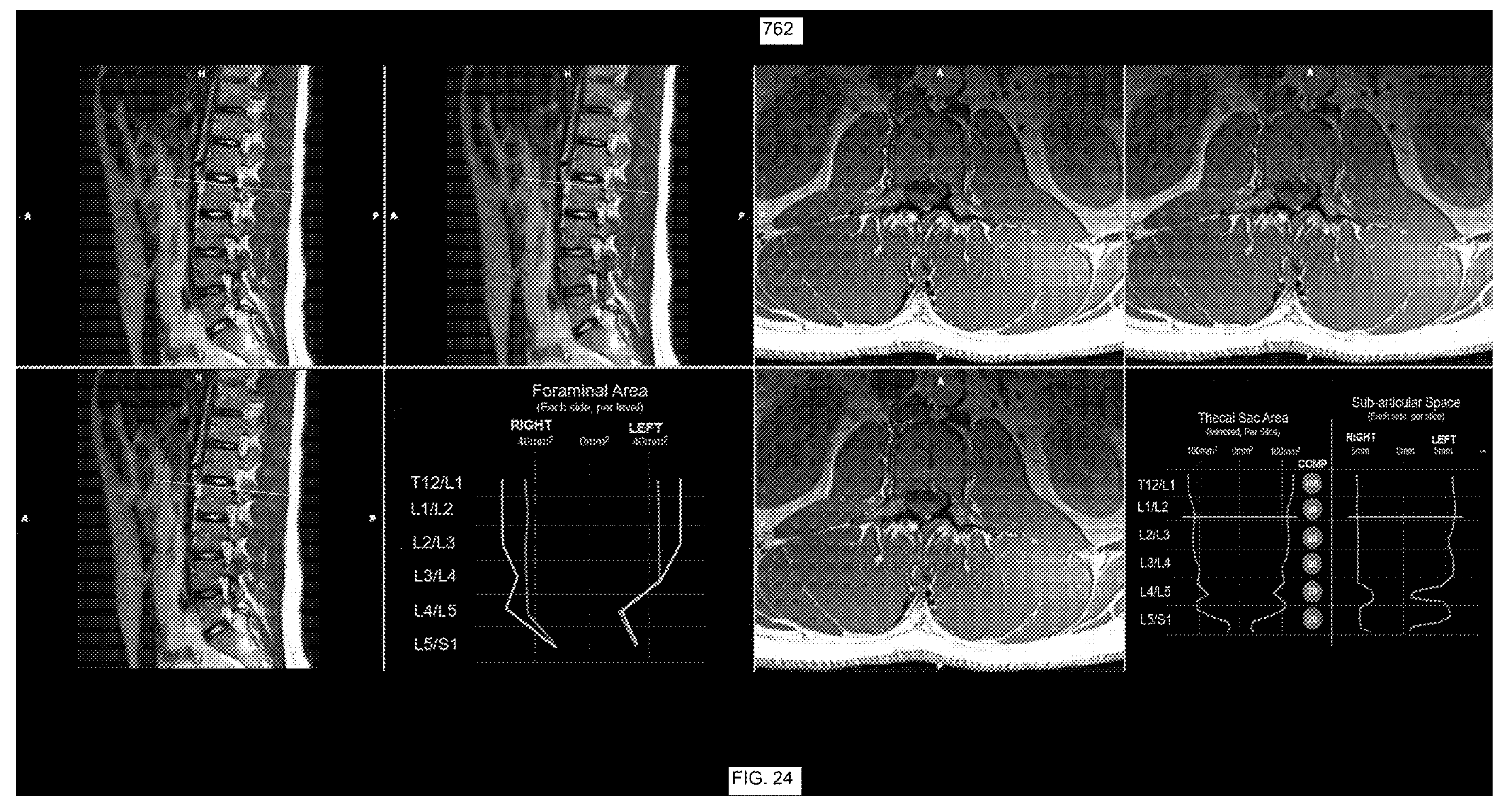
Figure 25:
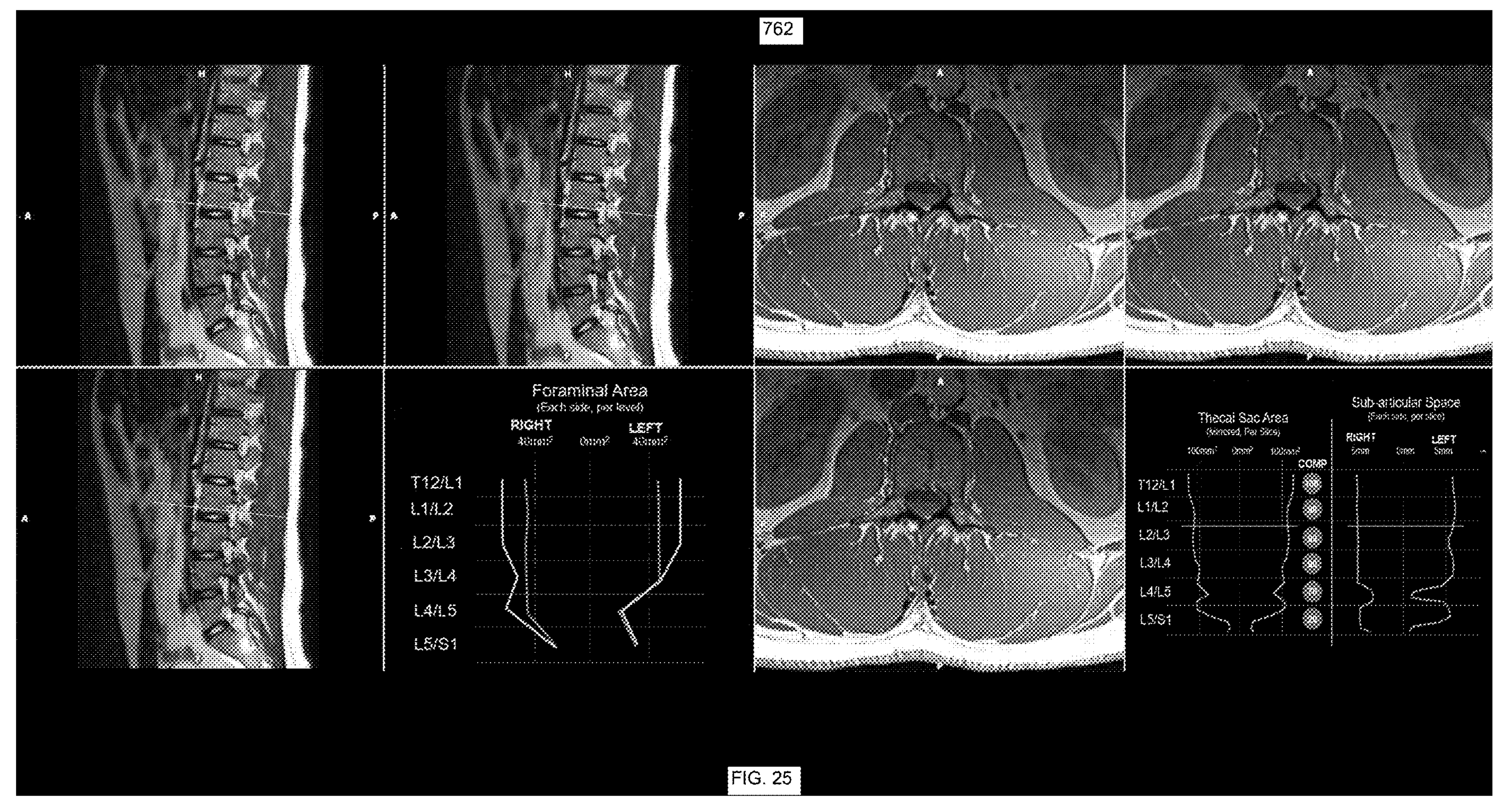
Figure 26:
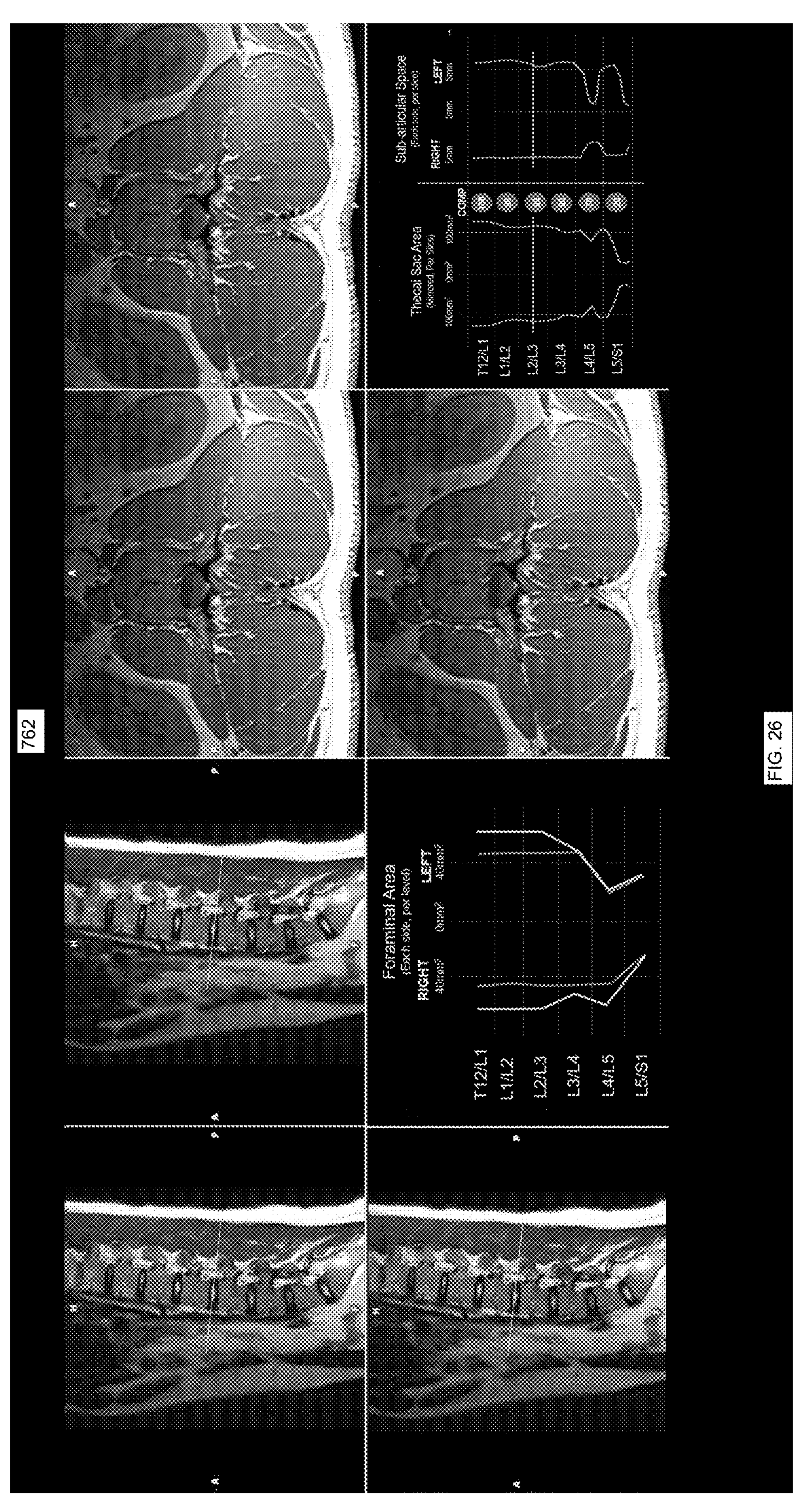
Figure 27:
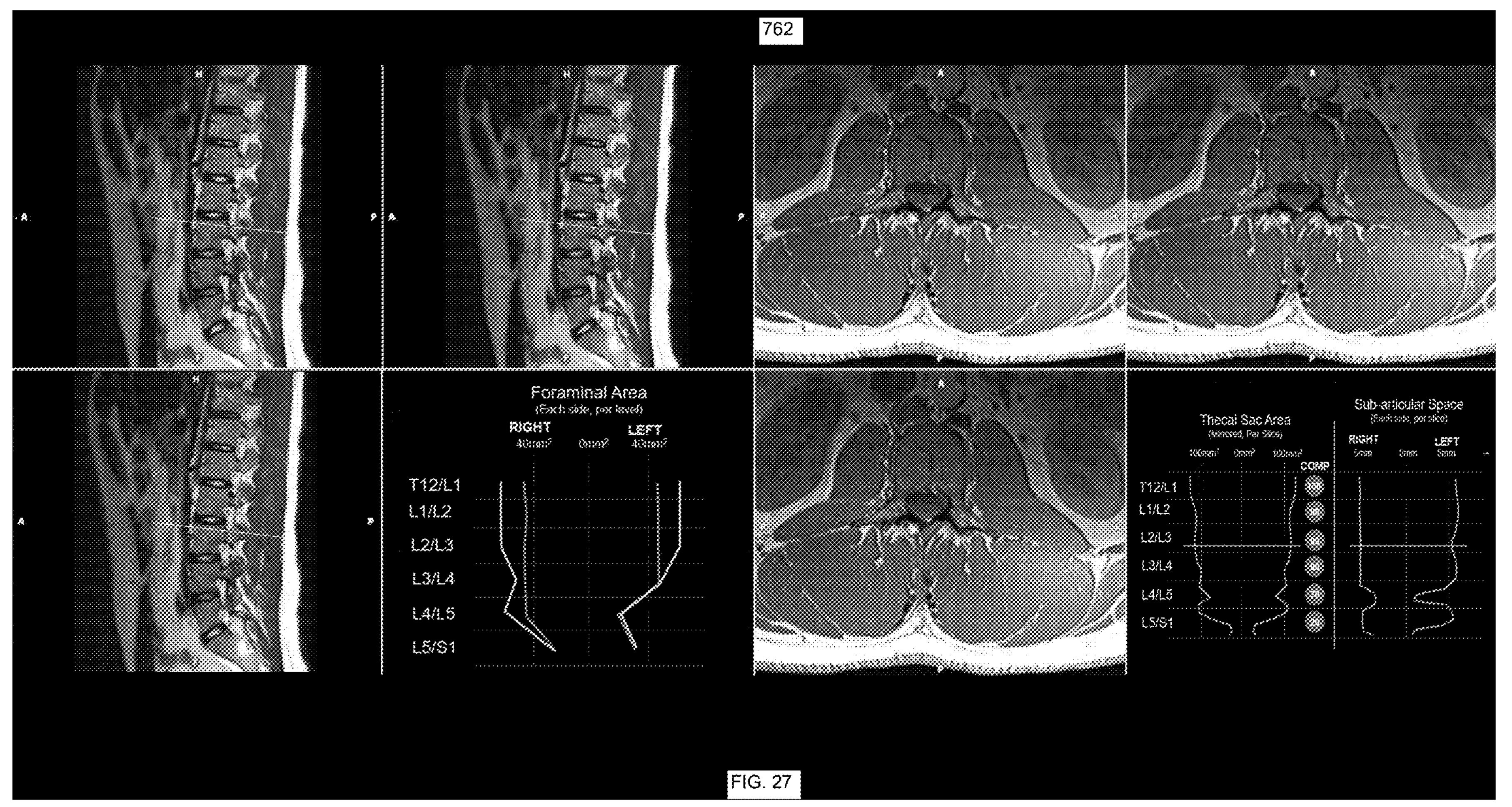
Figure 28:
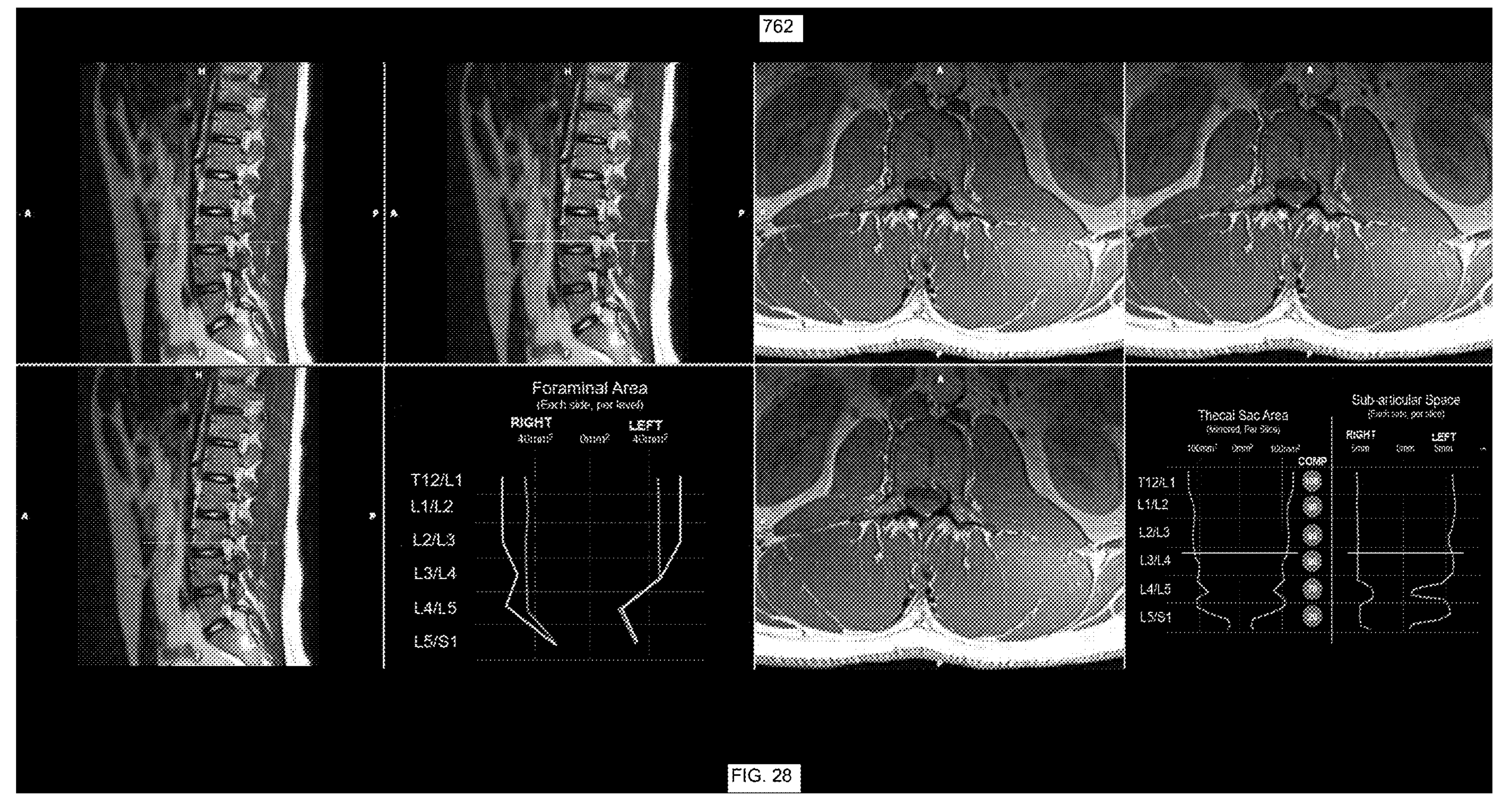
Figure 29:
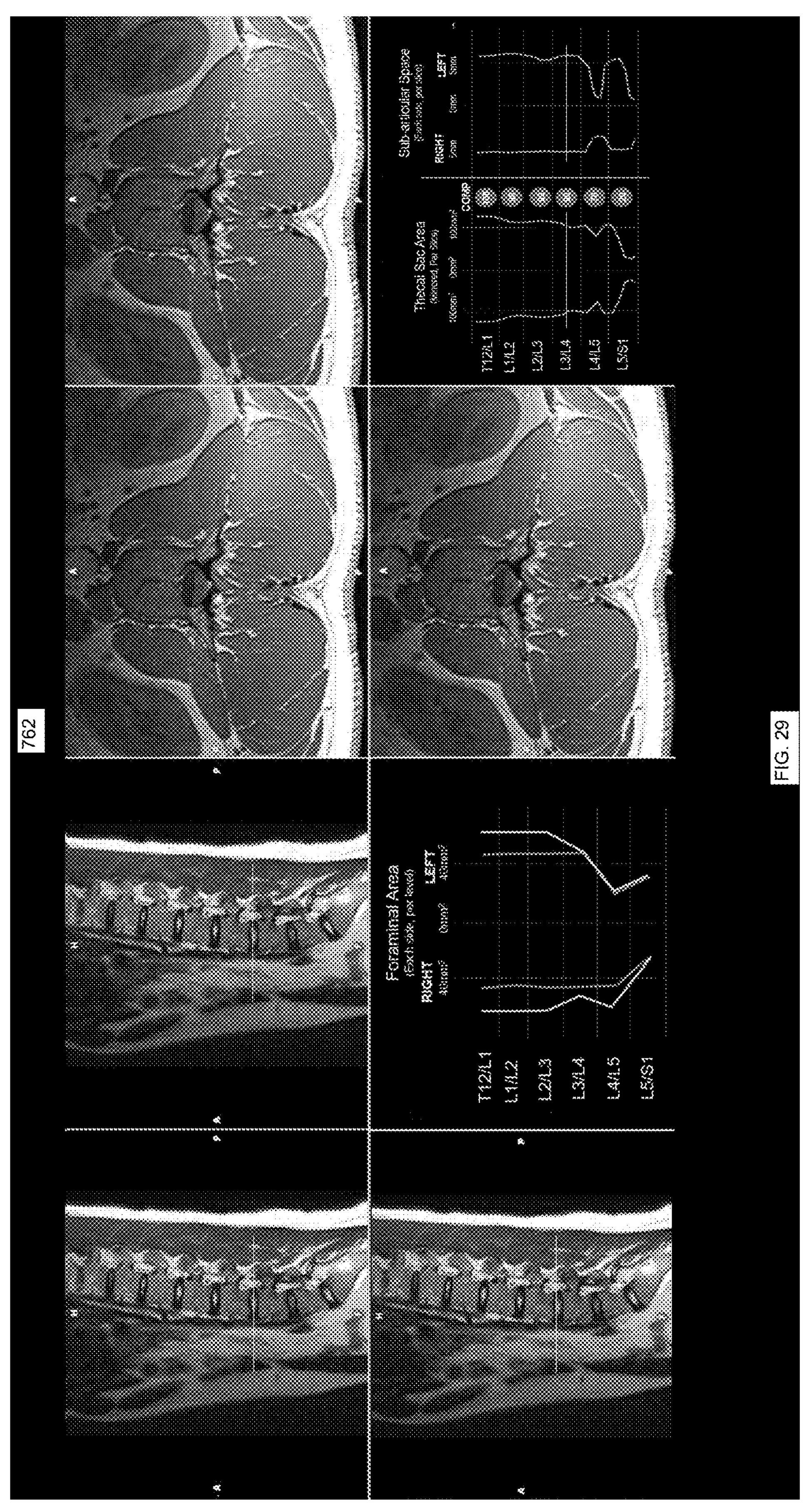
Figure 30:
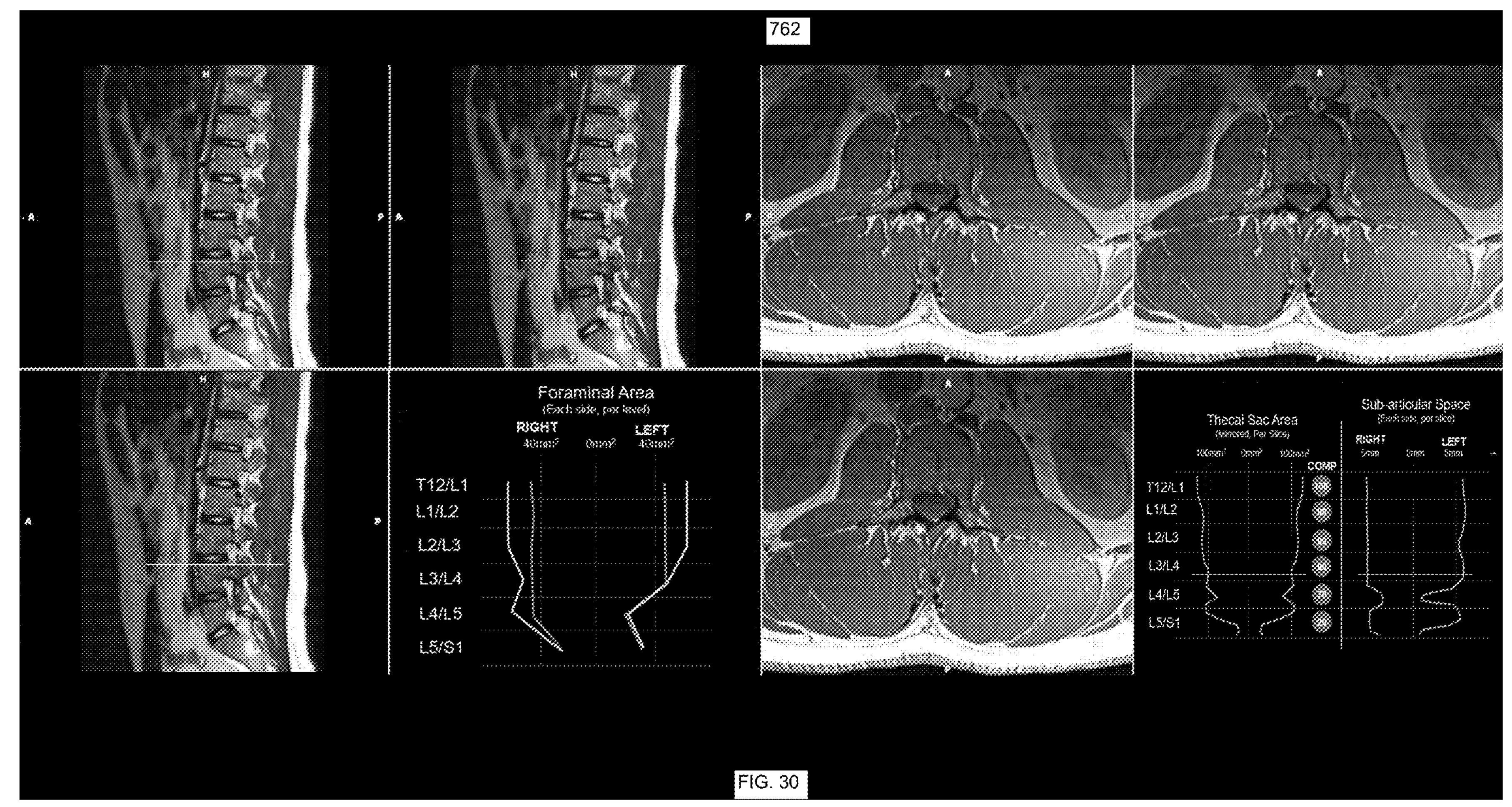
Figure 31:
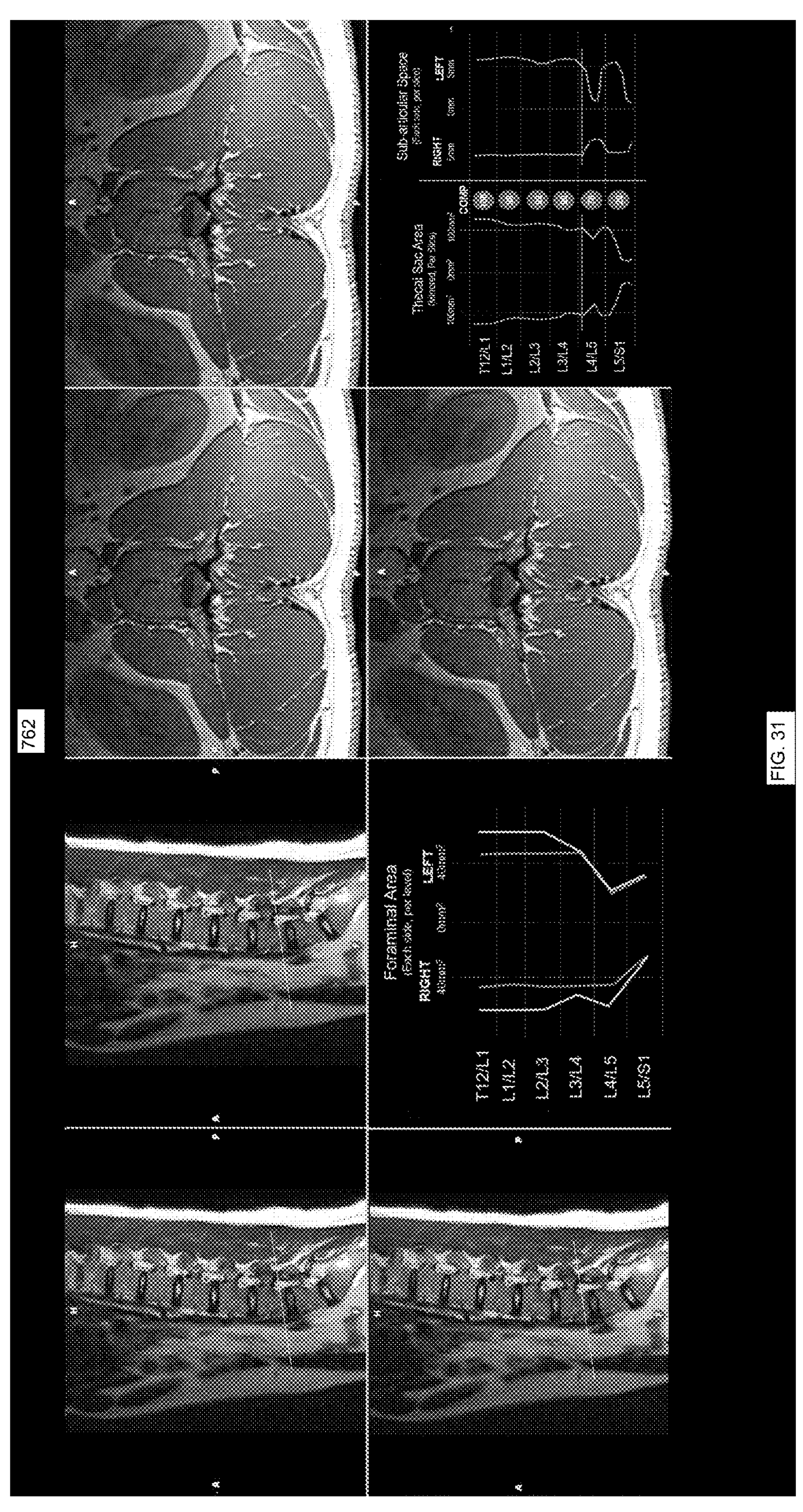
Figure 32:
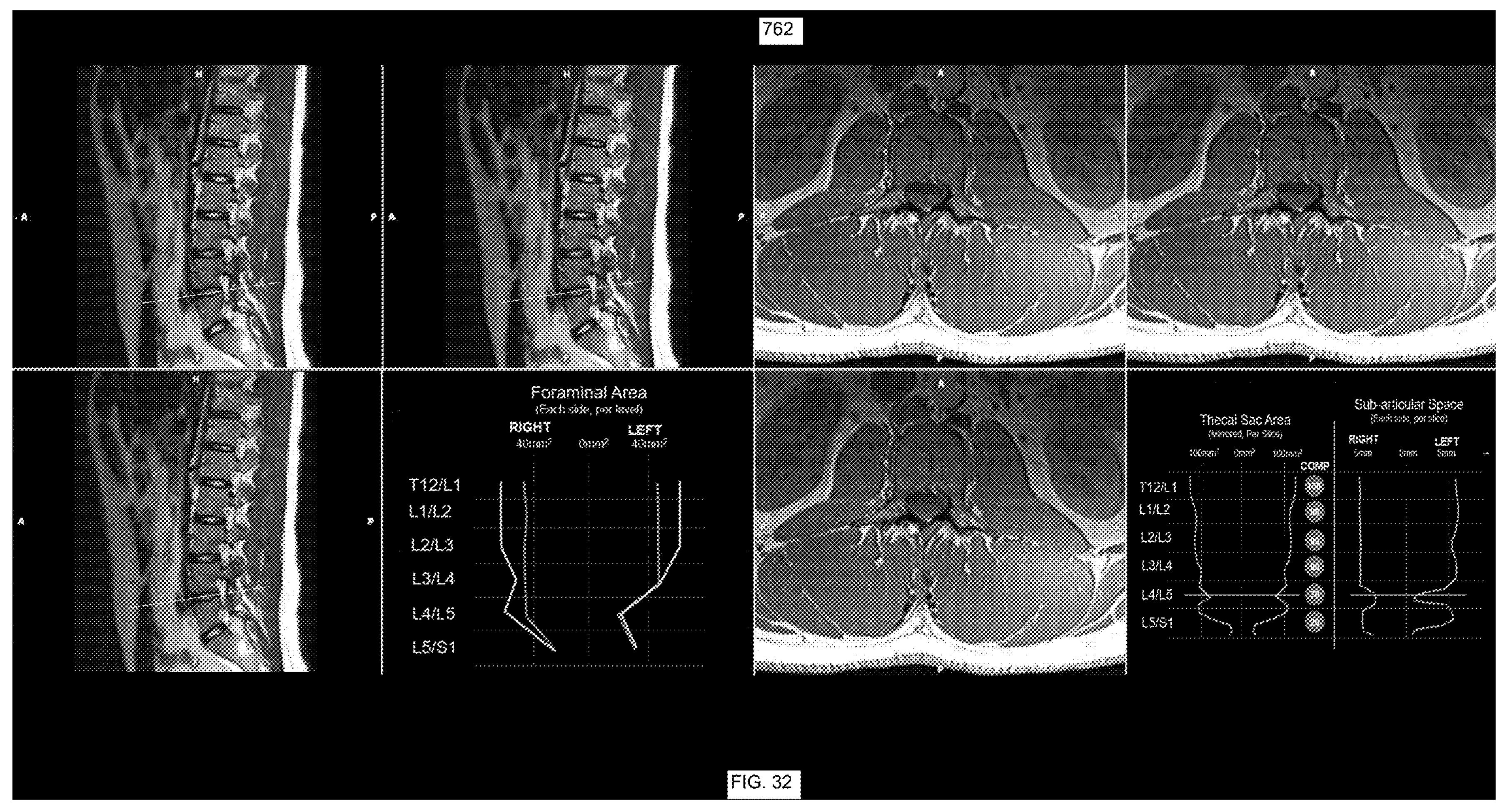
Figure 33:
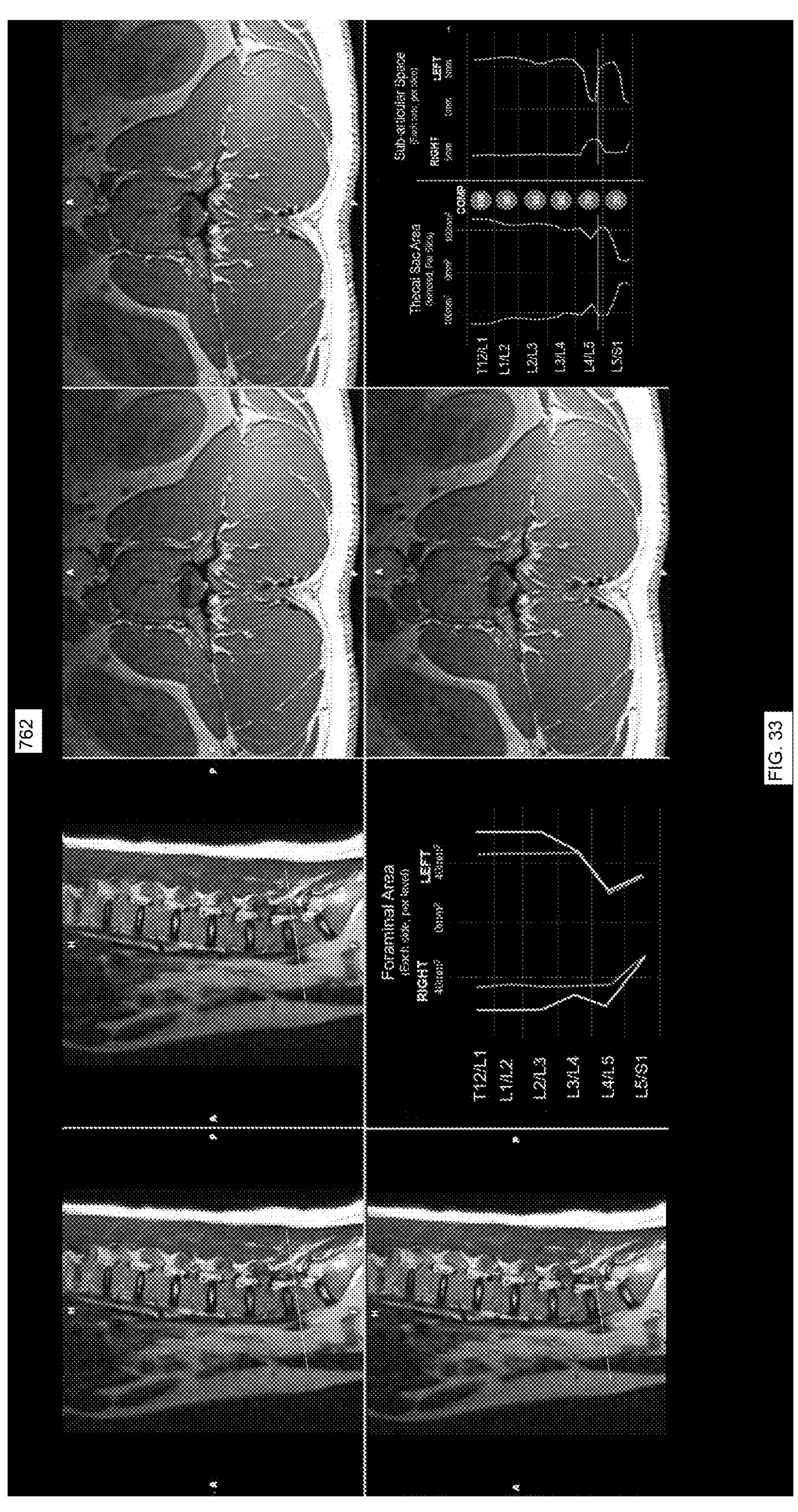
Figure 34:
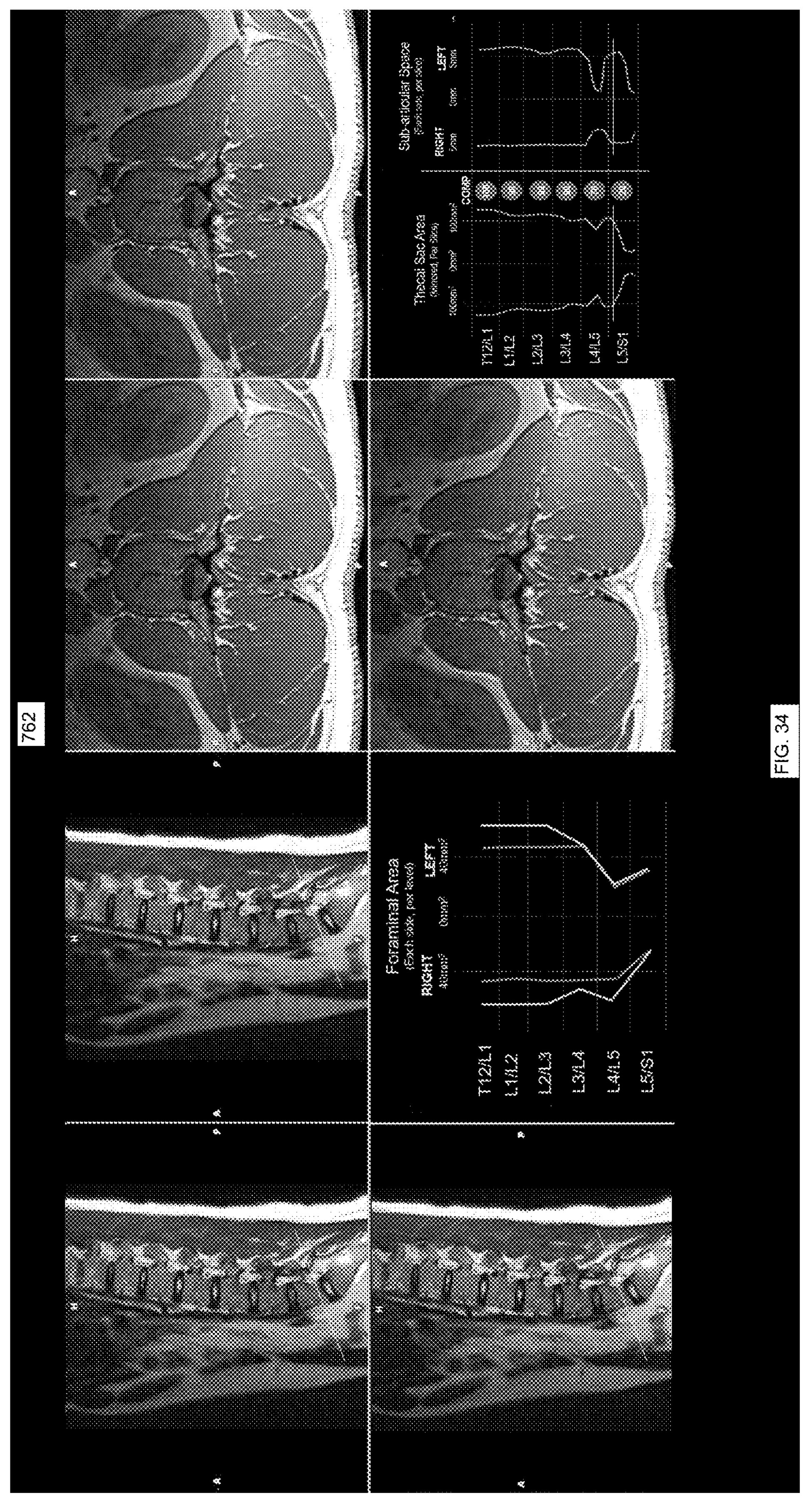
Figure 35:
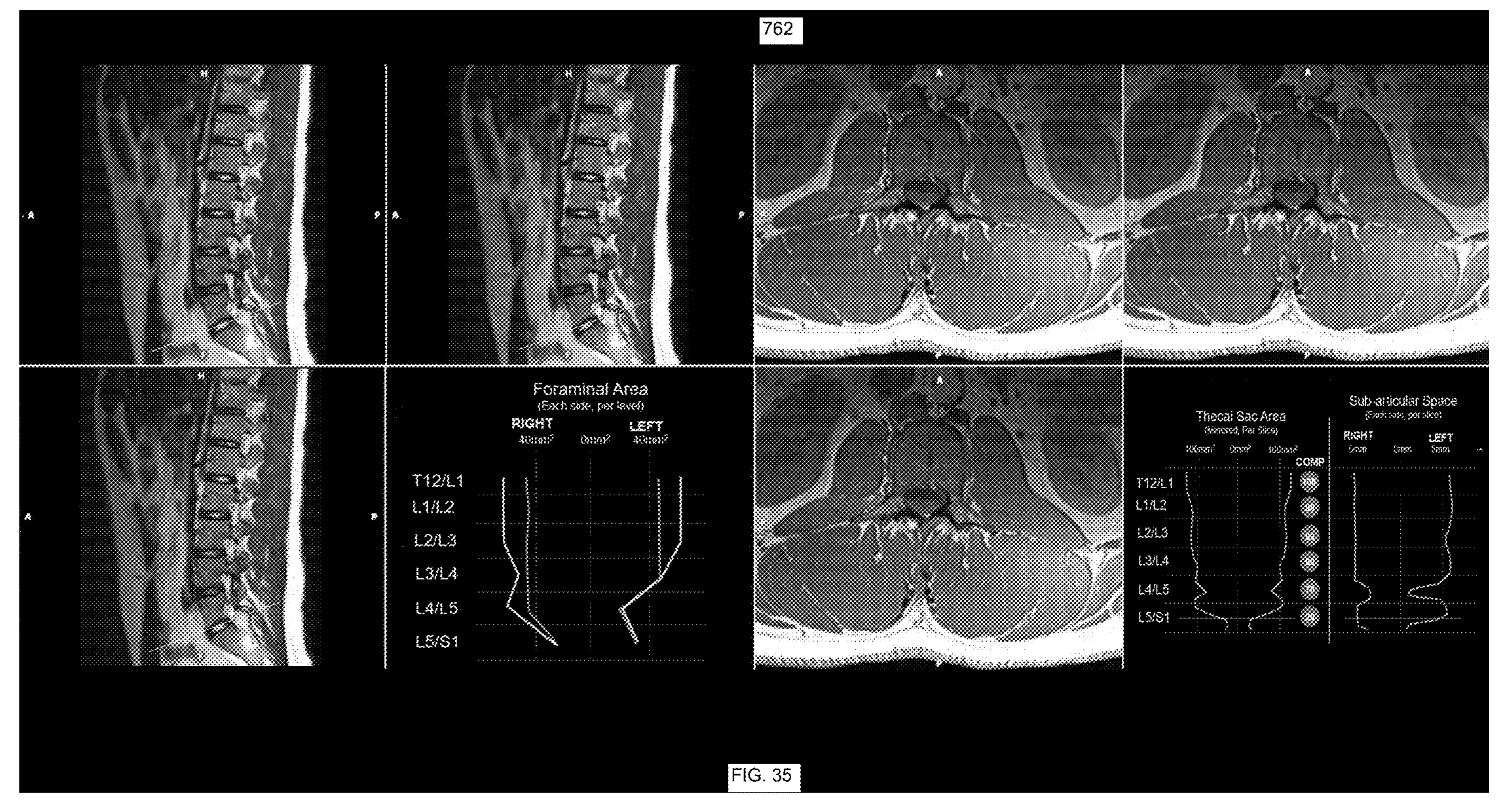
Figure 36:
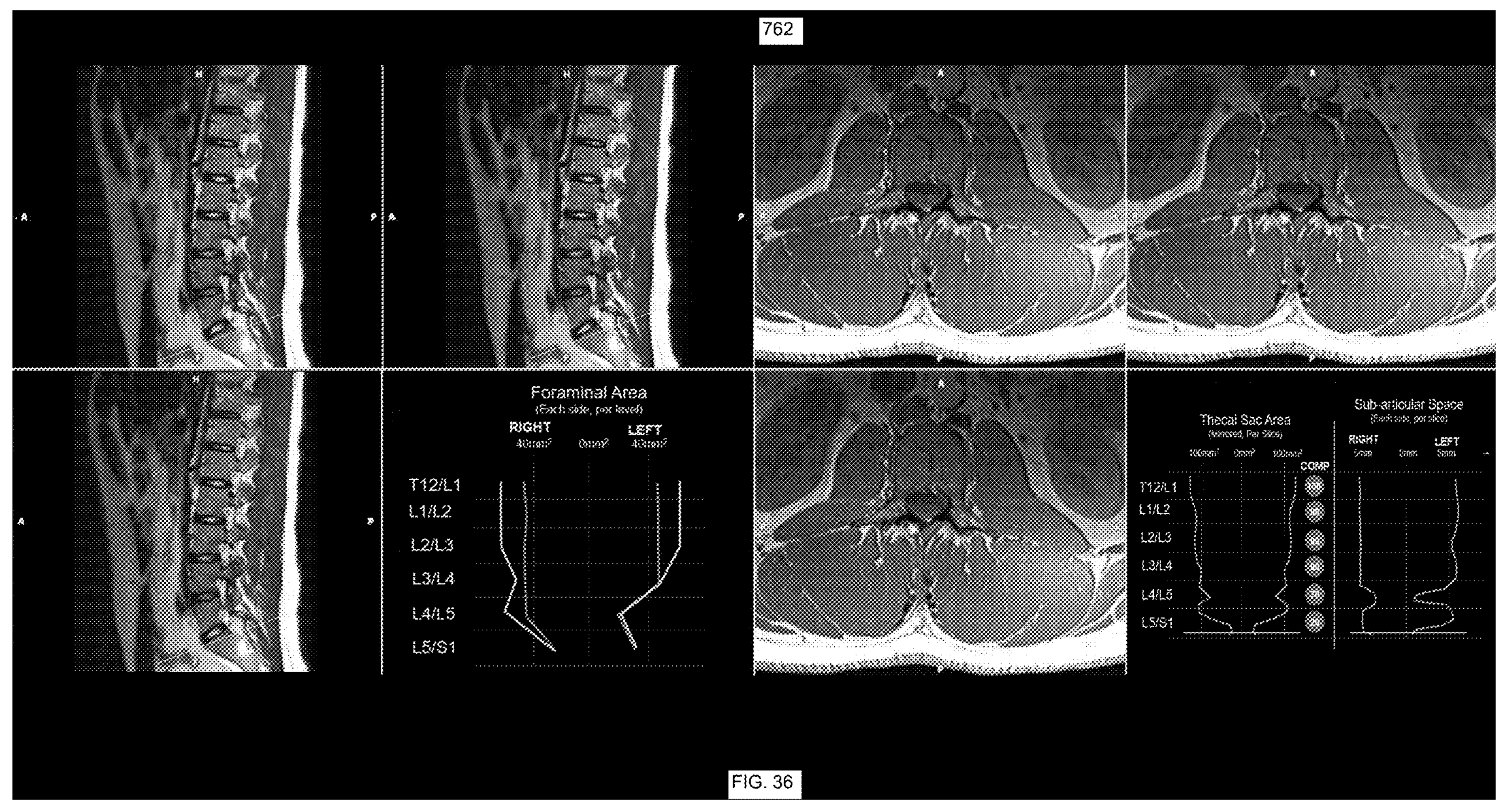
Figure 37:
FIGS. 37-40 are schematics illustrating a data visualization interface including a visualization of a data series representing quantitative data registered to imaging data, according to some embodiments.
Figure 38:
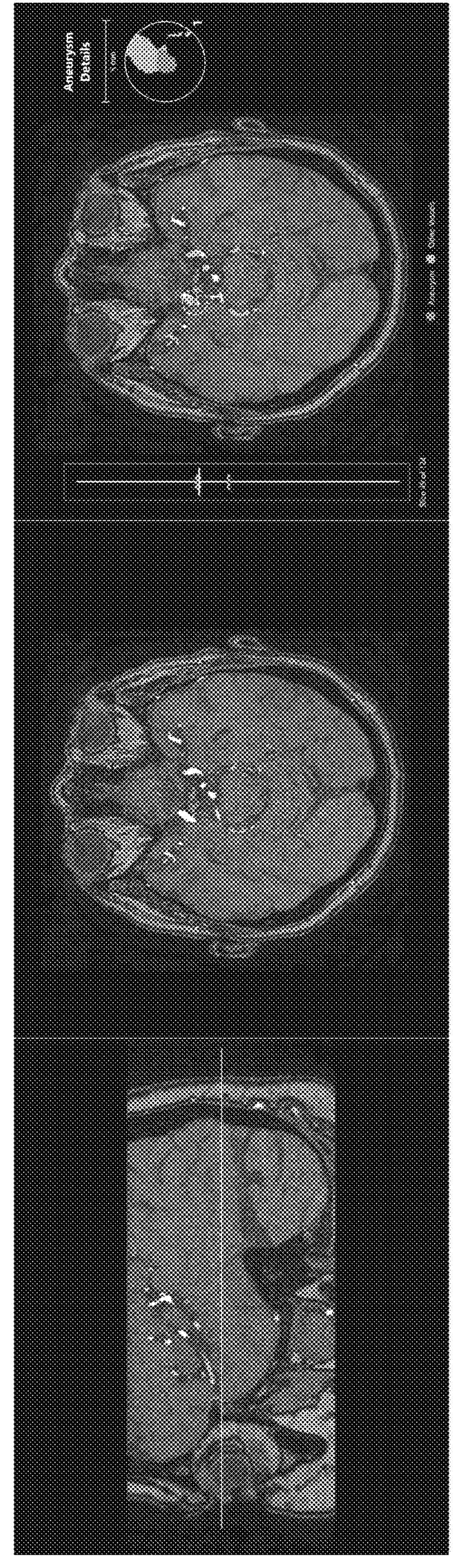
Figure 39:
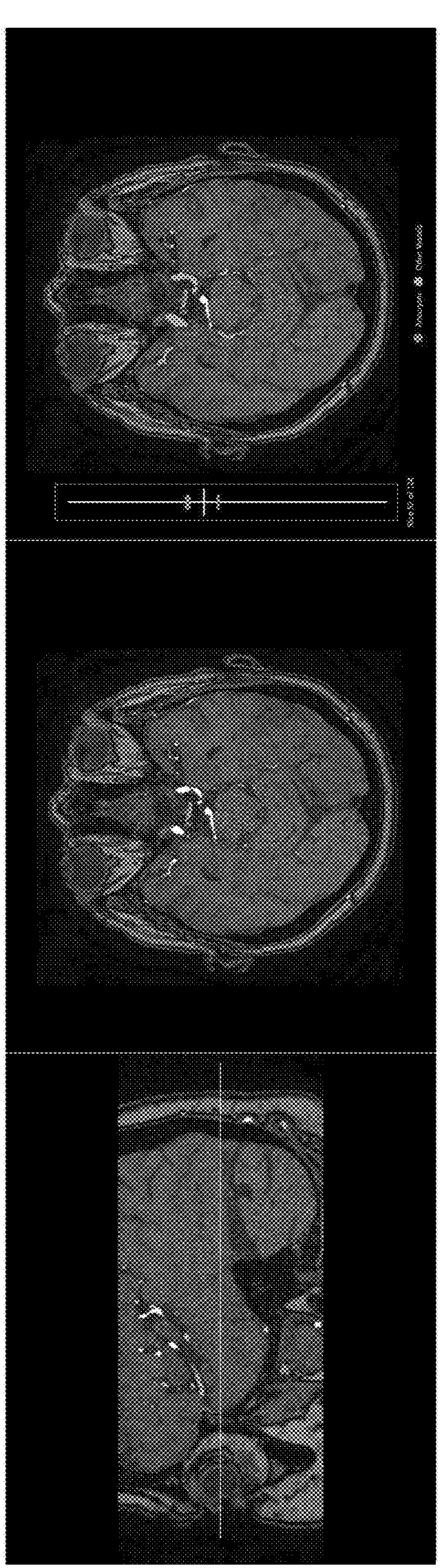
Figure 40:
Figure 41:
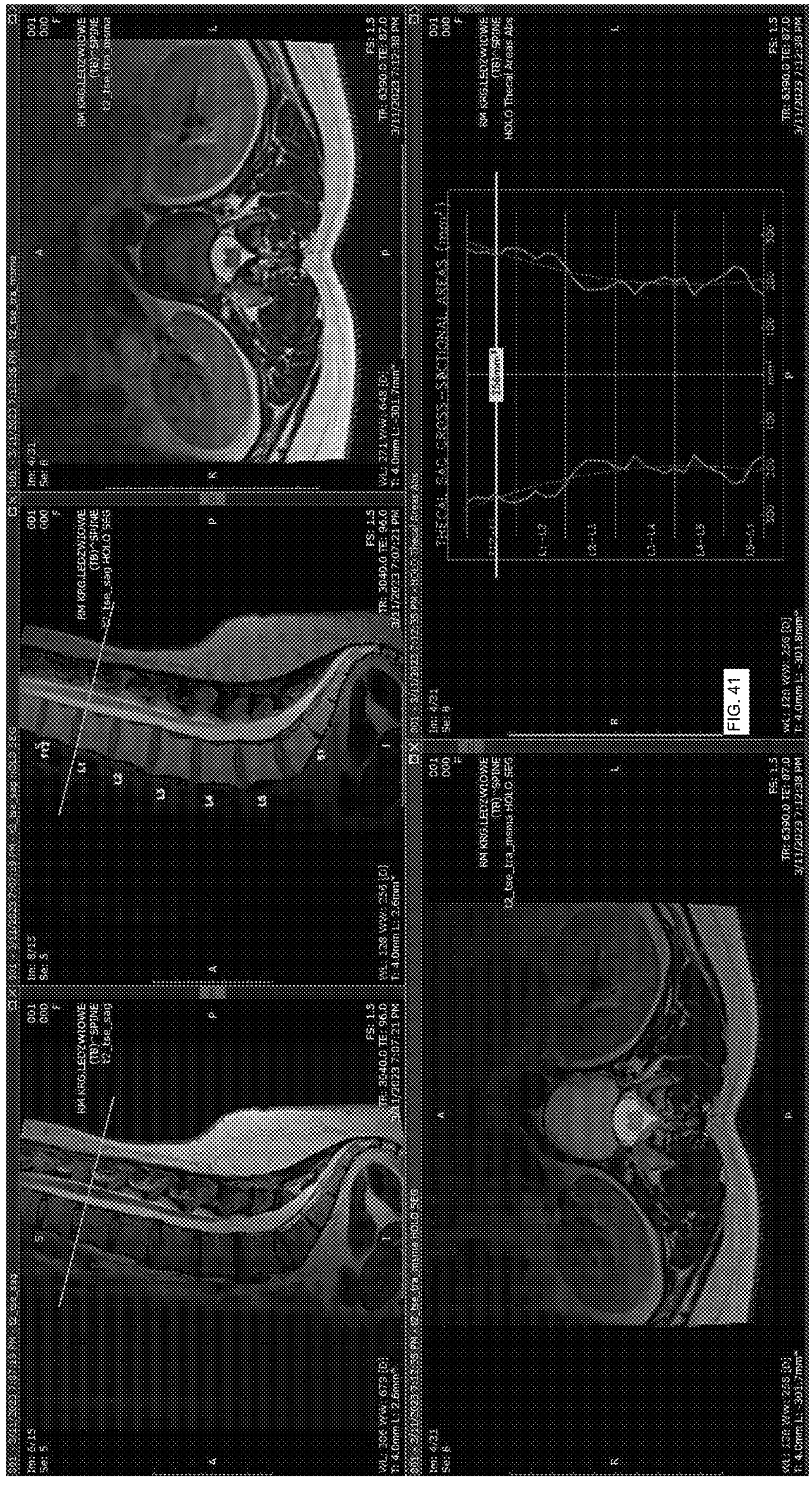
FIGS. 41-42 are schematics illustrating a data visualization interface including a visualization of a data series representing quantitative data registered to imaging data, according to some embodiments.
Figure 42:
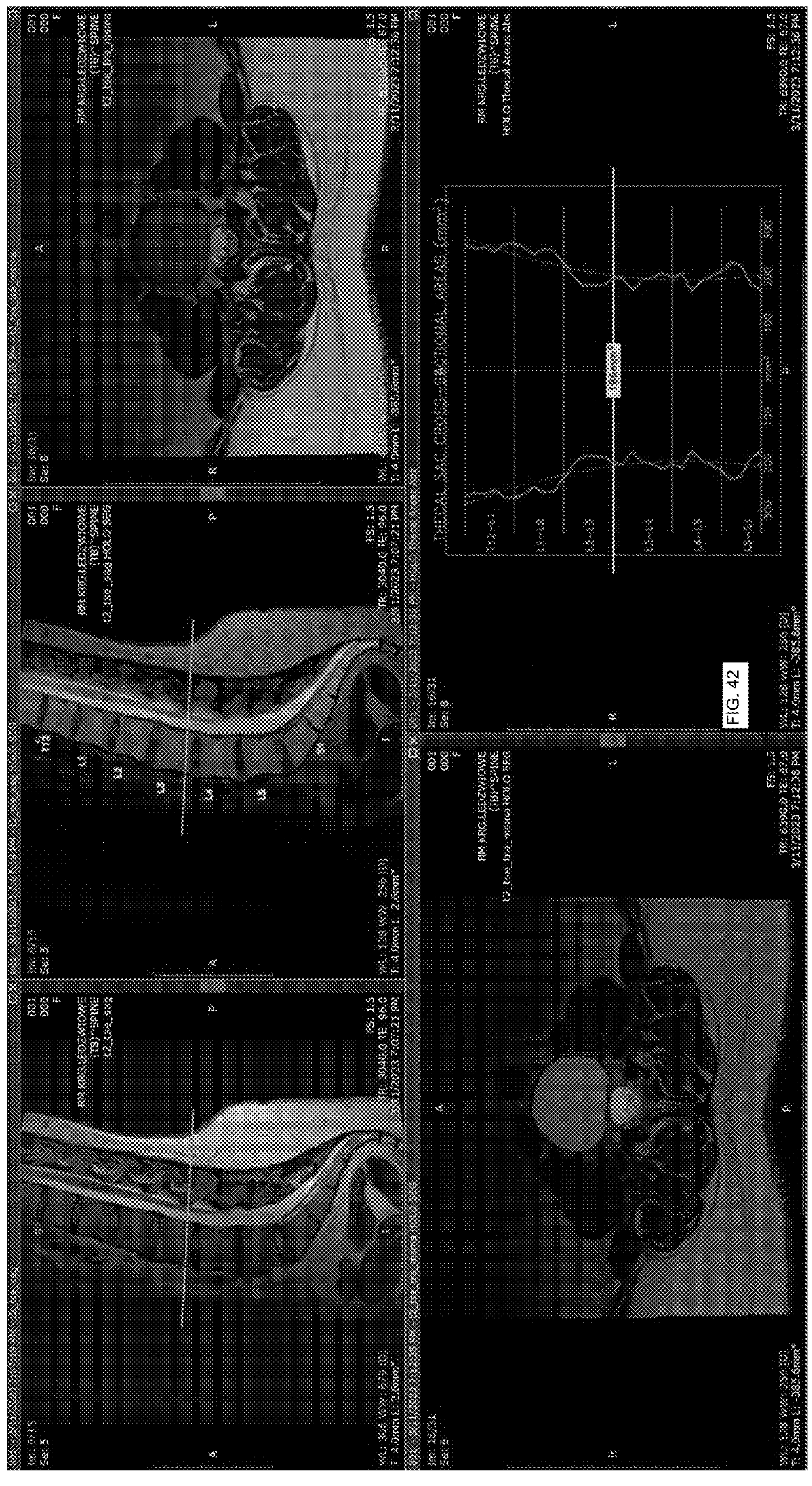

FIGS. 16A-16C, 17A-17C, and 18A-18C illustrate example depictions of quantitative data that can be represented via visualization of structured data as shown in the interface 662 via panel 664*c*, in some embodiments. FIGS. 16A-16C are example plots showing visualization of a data series representing quantitative data associated with measurements of the thecal sac area, sub-articular space, and foraminal area of a patients spinal cord, according to some embodiments. FIGS. 17A-17C are example plots showing visualization of a data series representing quantitative data associated with measurements of the ligamentum volume, facet volume, and epidural fat volume of a patients spinal cord, according to some embodiments. FIGS. 18A-18C example plots showing visualization of a data series representing quantitative data associated with measurements of the total disc volume, annulus volume, and nucleus volume of a patients spinal cord, according to some embodiments FIGS. 19-36 are schematics illustrating a data visualization interface 762 including visualization of multiple data series representing quantitative data (e.g., data representing foraminal area, thecal sac, and subarticular space) registered to imaging data, according to some embodiments. The interface 762 can be substantially similar in structure and/or function to the interface 662 described herein. As shown in FIGS. 6-15, the graphs depicting the data series representing foraminal area, thecal sac, and subarticular space include a marker that is positioned at a location on the graph that corresponds to the position of the currently viewed axial image at the position indicated in sagittal image. Scrolling from FIG. 19 to FIG. 36, the position of the axial image moves from a relatively rostral position in FIG. 19 to increasingly caudal position in FIGS. 20-36. With each change in axial image position, the marker in the sagittal image indicates the position of the axial image in the rostro-caudal axis, and the marker in the graphs shows the position on the graph along the y-axis, indicating the data point corresponding to that axial image location. The value of the data point is indicated along the x-axis of each graph.

FIGS. 37-40 are schematics illustrating a data visualization interface 962, including a visualization of a data series representing quantitative data registered to imaging data, according to some embodiments. The interface 972 can be substantially similar in structure and/or function to any of the interfaces described herein (e.g., interface 362, 562, 662, 762, and/or 862). As shown in the example implementation in FIGS. 37-40 the interface can be used to visualize brain imaging data along with non-image qualitative data co-registered with the brain imaging data, as described herein.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto: inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which examples have been provided. The acts performed as part of the methods may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

Some embodiments and/or methods described herein can be performed by a different software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Python, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The invention claimed is:

1. A system for processing image data of patient anatomy, the system comprising:

an imaging device configured to image anatomical structures of a patient and generate anatomical image data corresponding to the anatomical structures; and a compute device configured to perform anatomical analysis based on the anatomical image data received from the imaging device, wherein to perform the anatomical analysis, the compute device is configured to:

provide, to a segmentation analysis model, the anatomical image data, wherein the segmentation analysis model comprises a segmentation convolutional neural network (CNN) model;

receive, from the segmentation analysis model, segmentation of the anatomical image data identifying one or more anatomical parts of interest of the anatomical structures;

provide, to a level identification model, the anatomical image data, wherein the level identification model comprises a level identification CNN model;

receive, from the level identification model, a set of levels for different regions of a spine of the patient;

identify one or more anatomical features within the anatomical image data based on the one or more anatomical parts of interest and the set of levels for different regions, wherein the segmentation analysis model is selected based on a type of the imaging device or the level identification model is selected based on a type of the imaging device;

provide, to a spinal analysis model, the anatomical image data, wherein the spinal analysis model comprises a spinal CNN model; and receive, from the spinal analysis model, a classification of one or more anatomical structures captured in the anatomical image data, wherein the classification comprises an indication of a spinal condition or deformity.

2. The system of claim 1, wherein the level identification model further identifies one or more regions of a spine of the patient to generate the set of levels.

3. The system of claim 2, wherein the compute device is configured to associate the spinal condition or deformity to the one or more regions of the spine of the patient based on the set of levels.

4. The system of claim 1, wherein the set of levels comprise a spinal level type.

5. The system of claim 1, further comprising a surgical navigation system configured to generate structured data based on the anatomical image data.

6. The system of claim 5, wherein the surgical navigation system is further configured to visualize the structured data using a data visualization interface.

7. The system of claim 6, wherein the structured data visualizes the patient's anatomy, the set of levels and the one or more anatomical features.

8. The system of claim 1, wherein the spinal analysis model comprises a stenosis model, and the classification comprises a stenosis assessment.

9. The system of claim 1, wherein the spinal analysis model comprises a disc degeneration model, and the classification comprises a disc degeneration assessment.

10. The system of claim 1, wherein the anatomical analysis further comprises associating the indication of the spinal condition or deformity with at least one of the one or more anatomical features.

11. The system of claim 1, wherein the set of levels outputs comprise an ordinal identifier.

12. The system of claim 1, wherein the set of levels comprise a range of vertebral levels.

13. A method for processing image data of patient anatomy, the method comprising:

imaging, with an imaging device, anatomical structures of a patient;

generating, with the imaging device, anatomical image data corresponding to the anatomical structures; and performing, with a compute device, anatomical analysis of the anatomical image data received from the imaging device, the anatomical analysis comprising:

providing, to a segmentation analysis model, the anatomical image data, wherein the segmentation analysis model comprises a segmentation convolutional neural network (CNN) model, wherein the segmentation analysis model is selected based on a type of the imaging device;

receiving, from the segmentation analysis model, segmentation of the anatomical image data identifying one or more anatomical parts of interest of the anatomical structures;

providing, to a level identification model, the anatomical image data, wherein the level identification model comprises a level identification CNN model;

receiving, from the level identification model, a set of levels for different regions of a spine of the patient;

identifying one or more anatomical features within the anatomical image data based on the one or more anatomical parts of interest and the set of levels for different regions;

providing, to a spinal analysis model, the anatomical image data, wherein the spinal analysis model comprises a neural network model; and receiving, from the spinal analysis model, a classification of one or more anatomical structures captured in the anatomical image data, wherein the classification comprises an indication of a spinal condition or deformity.

14. The method of claim 13, wherein the level identification model further identifies one or more regions of a spine of the patient to generate the set of levels.

15. The method of claim 13, wherein the set of levels comprise a spinal level type, an ordinal identifier, or a range of vertebral levels.

16. The method of claim 13, further comprising associating, by the compute device, the spinal condition or deformity to the one or more anatomical features of the spine of the patient based on the set of levels.

17. The method of claim 13, further comprising generating, at a surgical navigation system, structured data based on the anatomical image data.

18. A method for processing image data of patient anatomy, the method comprising:

imaging, with an imaging device, anatomical structures of a patient;

generating, with the imaging device, anatomical image data corresponding to the anatomical structures; and performing, with a compute device, anatomical analysis of the anatomical image data received from the imaging device, the anatomical analysis comprising:

providing, to a segmentation analysis model, the anatomical image data, wherein the segmentation analysis model comprises a segmentation convolutional neural network (CNN) model;

receiving, from the segmentation analysis model, segmentation of the anatomical image data identifying one or more anatomical parts of interest of the anatomical structures;

providing, to a level identification model, the anatomical image data, wherein the level identification model comprises a level identification CNN model, wherein the level identification model is selected based on a type of the imaging device;

receiving, from the level identification model, a set of levels for different regions of a spine of the patient;

identifying one or more anatomical features within the anatomical image data based on the one or more anatomical parts of interest and the set of levels for different regions;

providing, to a spinal analysis model, the anatomical image data, wherein the spinal analysis model comprises a neural network model; and receiving, from the spinal analysis model, a classification of one or more anatomical structures captured in the anatomical image data, wherein the classification comprises an indication of a spinal condition or deformity.

19. The method of claim 18, further comprising generating structured data based on the anatomical image data with a surgical navigation system.

20. The method of claim 18, further comprising associating, by the compute device, the spinal condition or deformity to the one or more anatomical features of the spine of the patient based on the set of levels.

* * * * *